US011497802B2

(12) United States Patent
Bomchil et al.

(10) Patent No.: US 11,497,802 B2
(45) Date of Patent: Nov. 15, 2022

(54) **LIVE ATTENUATED HETEROLOGOUS VACCINE FOR *LEPTOSPIRA***

(71) Applicants: MERIAL INC., Duluth, GA (US); VETAGRO-SUP, Marcy l'Etoile (FR); INSTITUT PASTEUR, Paris (FR)

(72) Inventors: Natalia Ines Bomchil, Lyons (FR); Lionel Pierre Cupillard, Bourgoin Jallieu (FR); Celia Fontana, Lyons (FR); Pierre-Michel Guigal, Leyment (FR); Jerome Bouvet, Lyons (FR); Mathieu Picardeau, Paris (FR); Angeli Kodjo, Fleurieux sur l'arbresles (FR)

( * ) Notice: Subject to any disclaimer, the term of this patent is extended or adjusted under 35 U.S.C. 154(b) by 0 days.

(21) Appl. No.: 15/763,892

(22) PCT Filed: Oct. 5, 2016

(86) PCT No.: PCT/US2016/055508
§ 371 (c)(1),
(2) Date: Mar. 28, 2018

(87) PCT Pub. No.: WO2017/062460
PCT Pub. Date: Apr. 13, 2017

(65) Prior Publication Data

US 2018/0271966 A1 Sep. 27, 2018

Related U.S. Application Data

(60) Provisional application No. 62/239,136, filed on Oct. 8, 2015.

(51) Int. Cl.

| | |
|---|---|
| ***A61K 39/02*** | (2006.01) |
| ***C07K 14/20*** | (2006.01) |
| *A61K 39/00* | (2006.01) |

(52) U.S. Cl.
CPC .......... *A61K 39/0225* (2013.01); *C07K 14/20* (2013.01); *A61K 2039/522* (2013.01); *A61K 2039/552* (2013.01)

(58) Field of Classification Search
None
See application file for complete search history.

(56) References Cited

FOREIGN PATENT DOCUMENTS

| | | | |
|---|---|---|---|
| WO | WO-2015138549 A1 * | 9/2015 | ......... A61K 39/0225 |
| WO | WO20150138549 | 9/2015 | |

OTHER PUBLICATIONS

Srikram et al. 2011 (Cross-protective immunity against Leptospirosis elicited by a live, attenuated lipopolysaccharide mutant; JID 203: 870-879) (Year: 2011).*

Ren et al. 2003 (Uinque physiological and pathogenic features of Leptospira interrogans revelaed by whole-genome sequencing; Nature 422: 888-893). (Year: 2003).*

Toker et al. 1996 (Deletion Analysis of the FliM Flagellar Switch Protein of Salmonella typhimurium; Journal of Bacteriology 178(24): 7069-7079). (Year: 1996).*

Hardham et al. 1995 (Identification and sequences of the Treponema pallidum fliM, fliY, flip, fliQ, fliR and flhB' genes; Gene 166: 57-64) (Year: 1995).*

Li et al. 2010 (Inactivation of a putative flagellar motor switch protein FliG1 prevents Borrelia burgdorferi from swimming in highly viscous media and blocks its infectivity; Mol Microbiol. 75(6): 1563-1576) (Year: 2010).*

Liao et al. 2009 (Inactivation of the fliY gene encoding a flagellar motor switch protein attenuates mobility and virulence of Leptospira interrogans strain Lai; BMC Microbiology: 1-10). (Year: 2009).*

Lambert et al. 2012 (FlaA proteins in Leptospira interrogans are essential for motility and virulence by are not required for formation of the flagellum sheath; Infection and Immunity 80(6): 2019-2025 (Year: 2012).*

Srikram et al., 2011, "Cross-protective Immunity Against Leptospirosis Elicited by a Live, Attenuated Lipopolysaccharide Mutant", J. Infectious Diseases, 203(6): 870-879.

Yan et al., 2009, "Identification and characterization of OmpA-like proteins as novel vaccine candidates for Leptospirosis", Vaccine, 28(11): 2277-2283.

Zhang et al., 2013, "Leptospiral LruA is required for virulence and modulates an interaction with mammalian apolipoprotein AI", Infection and Immunity, 81(10): 3872-3879.

Fontana et al., 2016,"Analysis of a Spontaneous Non-Motile and Avirulent Mutant Shows That FliM Is Required for Full Endoflagella Assembly in Leptospira interrogans.", PLoS ONE 11(4): e0152916. https://doi.org/10.1371/joumal.pone.0152916.

Pappas CJ et al., 2015, "A replicative plasmid vector allows efficient complementation of pathogenic Leptospira strains", Appl. Environ. Microbiol., doi:10.1128/AEM.00173-15.

* cited by examiner

*Primary Examiner* — Mary Maille Lyons
(74) *Attorney, Agent, or Firm* — Jamie L. Graham

(57) ABSTRACT

The present invention provides compositions or vaccines that contain a recombinant or an attenuated *Leptospira interrogans* that elicit an immune response in animals against *Leptospira* infection, including compositions comprising said recombinant or attenuated *L. interrogans*, methods of vaccination against *Leptospira*, and kits for use with such methods and compositions.

21 Claims, 19 Drawing Sheets

Specification includes a Sequence Listing.

Figure 8A

**SEQ ID NO:15 DNA of *fliM* gene in strain Australis733 (WT) (the bold-underlined A at position 105 is missing in attenuated strain 702)**

ATGACAGAAATTTTATCCCAAGATGAAATTGACGCGTTACTTAGCGCCATCAGTTCCGGTGAAGTAAGCGAATCGG
ATTATGCTTCCGTTTCTGAACAAAAAAA<u>A</u>GTAAAGATCTACGATTTTAAACGTCCGGATAAATTTTCAAAAGACCAA
ATCCGTACTTTACAAATGATGCATGAAACCTTTGCACGTCTTGCAACCACAGGGCTTTCTGCTCAGCTAAGAGCGCT
TGTTTCGGTTCACGTTGCTTCTGTGGATCAGTTGACTTACGAAGAGTTCATTCGTTCCATTCCAAATCCCACAACACT
TGCAGTAATCAACATGGACCCTCTTAGAGGTTCTGCAATCTTAGAAATTGATCCATCAATTTCTTTTACGATCATCG
ATCGTCTGTTTGGTGGTAAAGGAGAACAGGCAAAAATTTCCAGGGAACTTTCTGAAATAGAAATGAGCGTAATGG
AAGGAATTATTGTAAGAATTTTAGGAAACATGAGAGAATCGTGGTCCACAGTGATAGACTTAAGACCTAGGCTTG
GAAACATTGAAACAAACCCTCAATTTGCTCAAGTAGTTCCTCCAAACGACATGGTGGTTTTGATTACTCTGGAAACT
AAAATCGGAGAAGTGGAAGGGATGACGAATCTTTGTATTCCTTATATCACGATCGAACCGATCATCAATAAACTAT
CAGCACAATATTGGTATTCTTCCATTCGTAAGGGAGAATTGGATGAAAACCGTGCCGTGATTCAGGAAAGATTGG
ATCAAGTAGCCATTCCTTTGATTGCGGAAGTTGGGTCTGTGGACGTTTCCATTAACGATTTTATGAATCTTTCTATT
GGAGATGTAGTAAAACTCGAAAACACTTCTACAAGATCAGAGATGATCGTAAAAGTAGGAGAAAGAAAAAAGTT
CAAATGCCTTCCTGGAAGAGTAGGAAGCAGACTCGCCATTCAGATCGGTGAAAGAGTAGAAGATATTCCAGATGA
ACTTTTGGGTTCTACTCGTTCTGAACAAGAATAT

**SEQ ID NO:16 mutated DNA of *fliM* gene in strain Australis702 (attenuated strain)**

ATGACAGAAATTTTATCCCAAGATGAAATTGACGCGTTACTTAGCGCCATCAGTTCCGGTGAAGTAAGCGAATCGG
ATTATGCTTCCGTTTCTGAACAAAAAAAGTAAAGATCTACGATTTTAAACGTCCGGATAAATTTTCAAAAGACCAAA
TCCGTACTTTACAAATGATGCATGAAACCTTTGCACGTCTTGCAACCACAGGGCTTTCTGCTCAGCTAAGAGCGCTT
GTTTCGGTTCACGTTGCTTCTGTGGATCAGTTGACTTACGAAGAGTTCATTCGTTCCATTCCAAATCCCACAACACTT
GCAGTAATCAACATGGACCCTCTTAGAGGTTCTGCAATCTTAGAAATTGATCCATCAATTTCTTTTACGATCATCGA
TCGTCTGTTTGGTGGTAAAGGAGAACAGGCAAAAATTTCCAGGGAACTTTCTGAAATAGAAATGAGCGTAATGGA
AGGAATTATTGTAAGAATTTTAGGAAACATGAGAGAATCGTGGTCCACAGTGATAGACTTAAGACCTAGGCTTGG
AAACATTGAAACAAACCCTCAATTTGCTCAAGTAGTTCCTCCAAACGACATGGTGGTTTTGATTACTCTGGAAACTA
AAATCGGAGAAGTGGAAGGGATGACGAATCTTTGTATTCCTTATATCACGATCGAACCGATCATCAATAAACTATC
AGCACAATATTGGTATTCTTCCATTCGTAAGGGAGAATTGGATGAAAACCGTGCCGTGATTCAGGAAAGATTGGA
TCAAGTAGCCATTCCTTTGATTGCGGAAGTTGGGTCTGTGGACGTTTCCATTAACGATTTTATGAATCTTTCTATTG
GAGATGTAGTAAAACTCGAAAACACTTCTACAAGATCAGAGATGATCGTAAAAGTAGGAGAAAGAAAAAAGTTCA
AATGCCTTCCTGGAAGAGTAGGAAGCAGACTCGCCATTCAGATCGGTGAAAGAGTAGAAGATATTCCAGATGAAC
TTTTGGGTTCTACTCGTTCTGAACAAGAATAT

Figure 8B

**SEQ ID NO:17 *fliM protein translated from wild-type DNA of fliM* in strain Australis733 (WT)**

Mteilsqdeidallsaissgevsesdyasvseqkkvkiydfkrpdkfskdqirtlqmmhetfarlattglsaqlralvsvhvasvdqltyeefirsipnpt tlavinmdplrgsaileidpsisftiidrlfggkgeqakisrelseiemsvmegiivrilgnmreswstvidlrprlgnietnpqfaqvvppndmvvlitl etkigevegmtnlcipyitiepiinklsaqywyssirkgeldenraviqerldqvaipliaevgsvdvsindfmnlsigdvvklentstrsemivkvger kkfkclpgrvgsrlaiqigervedipdellgstrseqey

**SEQ ID NO:18 truncated fliM protein translated from mutated DNA of *fliM* gene in strain Australis702 (attenuated strain)**

mteilsqdeidallsaissgevsesdyasvseqkk*

DNA sequence alignment

```
                      1                                                50
SEQ ID NO:15     (1)  ATGACAGAAATTTTATCCCAAGATGAAATTGACGCGTTACTTAGCGCCAT
SEQ ID NO:16     (1)  ATGACAGAAATTTTATCCCAAGATGAAATTGACGCGTTACTTAGCGCCAT

                      51                                              100
SEQ ID NO:15    (51)  CAGTTCCGGTGAAGTAAGCGAATCGGATTATGCTTCCGTTTCTGAACAAA
SEQ ID NO:16    (51)  CAGTTCCGGTGAAGTAAGCGAATCGGATTATGCTTCCGTTTCTGAACAAA

                      101                                             150
SEQ ID NO:15   (101)  AAAAAGTAAAGATCTACGATTTTAAACGTCCGGATAAATTTTCAAAAGAC
SEQ ID NO:16   (101)  AAAA-GTAAAGATCTACGATTTTAAACGTCCGGATAAATTTTCAAAAGAC

                      151                                             200
SEQ ID NO:15   (151)  CAAATCCGTACTTTACAAATGATGCATGAAACCTTTGCACGTCTTGCAAC
SEQ ID NO:16   (150)  CAAATCCGTACTTTACAAATGATGCATGAAACCTTTGCACGTCTTGCAAC

                      201                                             250
SEQ ID NO:15   (201)  CACAGGGCTTTCTGCTCAGCTAAGAGCGCTTGTTTCGGTTCACGTTGCTT
SEQ ID NO:16   (200)  CACAGGGCTTTCTGCTCAGCTAAGAGCGCTTGTTTCGGTTCACGTTGCTT

                      251                                             300
SEQ ID NO:15   (251)  CTGTGGATCAGTTGACTTACGAAGAGTTCATTCGTTCCATTCCAAATCCC
SEQ ID NO:16   (250)  CTGTGGATCAGTTGACTTACGAAGAGTTCATTCGTTCCATTCCAAATCCC

                      301                                             350
SEQ ID NO:15   (301)  ACAACACTTGCAGTAATCAACATGGACCCTCTTAGAGGTTCTGCAATCTT
SEQ ID NO:16   (300)  ACAACACTTGCAGTAATCAACATGGACCCTCTTAGAGGTTCTGCAATCTT

                      351                                             400
SEQ ID NO:15   (351)  AGAAATTGATCCATCAATTTCTTTTACGATCATCGATCGTCTGTTTGGTG
SEQ ID NO:16   (350)  AGAAATTGATCCATCAATTTCTTTTACGATCATCGATCGTCTGTTTGGTG
```

Figure 8C

```
                               401                                               450
SEQ ID NO:15    (401)  GTAAAGGAGAACAGGCAAAAATTTCCAGGGAACTTTCTGAAATAGAAATG
SEQ ID NO:16    (400)  GTAAAGGAGAACAGGCAAAAATTTCCAGGGAACTTTCTGAAATAGAAATG

                       451                                               500
SEQ ID NO:15    (451)  AGCGTAATGGAAGGAATTATTGTAAGAATTTTAGGAAACATGAGAGAATC
SEQ ID NO:16    (450)  AGCGTAATGGAAGGAATTATTGTAAGAATTTTAGGAAACATGAGAGAATC

                       501                                               550
SEQ ID NO:15    (501)  GTGGTCCACAGTGATAGACTTAAGACCTAGGCTTGGAAACATTGAAACAA
SEQ ID NO:16    (500)  GTGGTCCACAGTGATAGACTTAAGACCTAGGCTTGGAAACATTGAAACAA

                       551                                               600
SEQ ID NO:15    (551)  ACCCTCAATTTGCTCAAGTAGTTCCTCCAAACGACATGGTGGTTTTGATT
SEQ ID NO:16    (550)  ACCCTCAATTTGCTCAAGTAGTTCCTCCAAACGACATGGTGGTTTTGATT

                       601                                               650
SEQ ID NO:15    (601)  ACTCTGGAAACTAAAATCGGAGAAGTGGAAGGGATGACGAATCTTTGTAT
SEQ ID NO:16    (600)  ACTCTGGAAACTAAAATCGGAGAAGTGGAAGGGATGACGAATCTTTGTAT

                       651                                               700
SEQ ID NO:15    (651)  TCCTTATATCACGATCGAACCGATCATCAATAAACTATCAGCACAATATT
SEQ ID NO:16    (650)  TCCTTATATCACGATCGAACCGATCATCAATAAACTATCAGCACAATATT

                       701                                               750
SEQ ID NO:15    (701)  GGTATTCTTCCATTCGTAAGGGAGAATTGGATGAAAACCGTGCCGTGATT
SEQ ID NO:16    (700)  GGTATTCTTCCATTCGTAAGGGAGAATTGGATGAAAACCGTGCCGTGATT

                       751                                               800
SEQ ID NO:15    (751)  CAGGAAAGATTGGATCAAGTAGCCATTCCTTTGATTGCGGAAGTTGGGTC
SEQ ID NO:16    (750)  CAGGAAAGATTGGATCAAGTAGCCATTCCTTTGATTGCGGAAGTTGGGTC

                       801                                               850
SEQ ID NO:15    (801)  TGTGGACGTTTCCATTAACGATTTTATGAATCTTTCTATTGGAGATGTAG
SEQ ID NO:16    (800)  TGTGGACGTTTCCATTAACGATTTTATGAATCTTTCTATTGGAGATGTAG

                       851                                               900
SEQ ID NO:15    (851)  TAAAACTCGAAAACACTTCTACAAGATCAGAGATGATCGTAAAAGTAGGA
SEQ ID NO:16    (850)  TAAAACTCGAAAACACTTCTACAAGATCAGAGATGATCGTAAAAGTAGGA

                       901                                               950
SEQ ID NO:15    (901)  GAAAGAAAAAAGTTCAAATGCCTTCCTGGAAGAGTAGGAAGCAGACTCGC
SEQ ID NO:16    (900)  GAAAGAAAAAAGTTCAAATGCCTTCCTGGAAGAGTAGGAAGCAGACTCGC

                       951                                              1000
SEQ ID NO:15    (951)  CATTCAGATCGGTGAAAGAGTAGAAGATATTCCAGATGAACTTTTGGGTT
SEQ ID NO:16    (950)  CATTCAGATCGGTGAAAGAGTAGAAGATATTCCAGATGAACTTTTGGGTT

                       1001                  1023
SEQ ID NO:15   (1001)  CTACTCGTTCTGAACAAGAATAT
SEQ ID NO:16   (1000)  CTACTCGTTCTGAACAAGAATAT
```

Figure 8D

Protein sequence alignment

```
                     1                                 35             50
SEQ ID NO:18    (1)  MTEILSQDEIDALLSAISSGEVSESDYASVSEQKK---------------
SEQ ID NO:17    (1)  MTEILSQDEIDALLSAISSGEVSESDYASVSEQKKVKIYDFKRPDKFSKD

                     51                                              100
SEQ ID NO:18   (36)  --------------------------------------------------
SEQ ID NO:17   (51)  QIRTLQMMHETFARLATTGLSAQLRALVSVHVASVDQLTYEEFIRSIPNP

                     101                                             150
SEQ ID NO:18   (36)  --------------------------------------------------
SEQ ID NO:17  (101)  TTLAVINMDPLRGSAILEIDPSISFTIIDRLFGGKGEQAKISRELSEIEM

                     151                                             200
SEQ ID NO:18   (36)  --------------------------------------------------
SEQ ID NO:17  (151)  SVMEGIIVRILGNMRESWSTVIDLRPRLGNIETNPQFAQVVPPNDMVVLI

                     201                                             250
SEQ ID NO:18   (36)  --------------------------------------------------
SEQ ID NO:17  (201)  TLETKIGEVEGMTNLCIPYITIEPIINKLSAQYWYSSIRKGELDENRAVI

                     251                                             300
SEQ ID NO:18   (36)  --------------------------------------------------
SEQ ID NO:17  (251)  QERLDQVAIPLIAEVGSVDVSINDFMNLSIGDVVKLENTSTRSEMIVKVG

                     301                                     341
SEQ ID NO:18   (36)  -----------------------------------------
SEQ ID NO:17  (301)  ERKKFKCLPGRVGSRLAIQIGERVEDIPDELLGSTRSEQEY
```

Figure 9

| SEQ ID NO: | type | Gene Description |
|---|---|---|
| 1 | DNA | PflgA : TAATACCCGAGCTTCAAGGAAG |
| 2 | DNA | FliMR2 : TAACTTCAATTCTAATATTCTTGTTCAGAACG |
| 3 | DNA | CF109 : CAATCGTGCTGAAGAATCTGAAAGAG |
| 4 | DNA | CF099 : CTGTAGCACAAGCCTGATTCGC |
| 5 | DNA | CF108 : TCCCAAGATGAAATTGACGCG |
| 6 | DNA | CF103 : CTACTCTTTCACCGATCTGAATGGC |
| 7 | DNA | flaB4F : CTCATATTTGCTTGTGCGAGC |
| 8 | DNA | flaB4R : GAACGCTACTGGTTTACAATTAGTTGC |
| 9 | DNA | rpoBF : ATGGAGCGGAACGTGTAGTC |
| 10 | DNA | rpoBR : CTTCGTTCGTTCCATGTCCT |
| 11 | DNA | FlimF: CGACACATATGACAGAAATTTTAT |
| 12 | DNA | FlimR2: TAACTTCAATTCTAATATTCTTGTTCAGAACG |
| 13 | DNA | *fliM* original sequence: GTT TCT GAA CAA AAA AAA GTA AAG ATC TAC GAT TTT |
| 14 | DNA | *fliM* mutated sequence GTT TCT GAA CAA AAA AAG TAA AGA TCT ACG ATT TTA |
| 15 | DNA | DNA of wild-type *fliM gene in* strain Australis733 (WT) |
| 16 | DNA | DNA of mutated *fliM gene in* strain Australis702 (attenuated) |
| 17 | protein | fliM protein of wild-type *fliM gene in* strain Australis733 (WT) |
| 18 | protein | fliM protein translated from mutated fliM *in* strain Australis702 (attenuated) |
| 19 | protein | Translation of *fliM* original sequence: VSEQKKVKIYDF |
| 20 | protein | Translation of *fliM* mutated sequence: VSEQKK |

IL 17 response in vaccinated dogs (V) and unvaccinated controls (Ctl)

ASAT

Creatinemia

Uremia

ALAT

LIVE ATTENUATED HETEROLOGOUS VACCINE FOR *LEPTOSPIRA*

CROSS-REFERENCE TO RELATED APPLICATIONS

This application claims priority to U.S. provisional application 62/239,136 filed on Oct. 8, 2015.

FIELD OF THE INVENTION

The present disclosure relates to live attenuated vaccines that provide heterologous protection from infection by *Leptospira* spirochetes. The present invention also relates to reagents and methods allowing their detection, methods of vaccination as well as methods of producing these reagents and vaccines.

BACKGROUND

Leptospirosis is a life-threatening disease representing the most spread zoonosis worldwide, affecting every mammalian species to include humans (B. Adler, 2015, *Leptospira* and *Leptospirosis*, vol. 387, B. Adler, Ed. Berlin, Heidelberg: Springer Berlin Heidelberg, pp. 1-9). This neglected and emerging infection is caused by the spirochete *Leptospira*, a helically-shaped bacteria with characteristic hook and spiral-shaped ends (Charon N W et al., 2002, Annu. Rev. Genet., vol. 36, no. 1, pp. 47-73). Infection with one of the 10 pathogenic species, including *Leptospira interrogans*, can result in a broad spectrum of symptoms from subclinical infection to multiple organ failure with a mortality rate of 10 to 50%. However, there is a considerable deficit in the understanding of basic aspects of the biology and virulence mechanisms of pathogenic *Leptospira*. This is mainly due to the lack of adequate and efficient genetic tools for these slow-growing bacteria. Therefore, only a limited number of virulence factors have been identified so far. Virulence mechanisms that have been described include pathogen adhesion and persistence in the host, host tissue damage, renal colonization, and pathogen entry and dissemination in the host (Murray G L, 2015, Curr. Top. Microbiol. Immunol., vol. 387, pp. 139-185).

The motility of spirochetes is unique in that they can swim in highly viscous gel-like media that slow or stop the motility of other peritrichously flagellated bacteria (C. Li et al., 2000, J. Mol. Microbiol. Biotechnol., vol. 2, no. 4, pp. 345-354). This motility is conferred by two endoflagella inserted subterminally in the periplasm at each pole, extending toward the middle of the cell without overlapping. Whether the poles are hook or spiral-shaped is defined by flagella rotation direction. Rotation in counterclockwise direction (CCW, as seen from the center of the cell) forms the spiral-shaped ends whereas rotation in clockwise direction (CW) results in hook-shaped ends. Symmetric rotation of flagella leads to non-translational motility. Translational motility only occurs when flagella are rotating in opposite direction, with the anterior end in hook-shape and the posterior end in corkscrew shape (Charon N W et al., 2002, supra).

Flagella of model systems *Escherichia coli* and *Salmonella enterica* have been widely studied (Berg H C, 2003, *Annu. Rev. Biochem.*, vol. 72, pp. 19-54; Macnab R M, 2003, Annu. Rev. Microbiol., vol. 57, pp. 77-100; Terashima H et al., 2008, Int. Rev. Cell Mol. Biol., vol. 270, pp. 39-85; S. Kojima S et al., 2004, Int. Rev. Cytol., vol. 233, pp. 93-134; Sowa Y et al., 2008, *Q. Rev. Biophys.*, vol. 41, no. 2, pp. 103-132). They are classically composed of a filament, a hook and a motor constituting the basal body, and their structure seems to be highly conserved within the bacterial kingdom (Zhao X et al., 2014, *Biochemistry* (*Most.*), vol. 53, no. 27, pp. 4323-4333). The flagellar filaments of spirochetes, however, are not composed of a single flagellin polymer like in enterobacteria, but comprise a complex structure of several subunits (Slamti L et al., 2011, *J. Bacteriol.*, vol. 193, no. 22, pp. 6266-6275). In *Leptospira*, site-directed or random mutagenesis allowed the study of some endoflagellum components, including the flagellar proteins FlaA, FlaB (Picardeau M et al., 2001, Mol. Microbiol., vol. 40, no. 1, pp. 189-199; Lambert A et al., 2012, Infect. Immun., vol. 80, no. 6, pp. 2019-2025), as well as FliY, a protein involved in flagellar motor and likely a part of the C-ring (Zhao X et al., 2014, supra; Liao S et al., 2009, BMC Microbiol., vol. 9, no. 1, p. 253). Cryo-electron tomography of *Leptospira* spp. also provides insights of the structure of the endoflagellum (Zhao X et al., 2014, supra; Zhao X et al., 2013, PNAS, vol. 110, no. 35, pp. 14390-14395; Raddi G et al., 2012, *J. Bacteriol.*, vol. 194, no. 6, pp. 1299-1306). Zhao and coworkers showed that leptospiral flagellar motor is composed of the MS ring (the base of the motor), the C ring, responsible for switch of motor rotation, the rod with L and P rings connecting the MS ring to the hook, a spirochete-unique structure called the collar surrounding the MS-ring, a complex export apparatus responsible for flagellar type III proteins including subunits of the rod, the hook and the filament, and finally the stator, which is the motor force generator. It is thought that C-ring is composed in its center of FliM in complex with FliN. Chemotaxis signaling protein CheY-P (CheY phosphorylated) binds to FliM and possibly FliN, leading by direct interaction to conformational change of FliG, rearranging the interaction between FliG and the stator, allowing switch rotation direction of the motor either in CW or CCW direction (Ahn D R et al., 2013, Int. J. Biol. Macromol., vol. 54, pp. 76-83; Y. Morimoto Y et al., 2014, Biomolecules, vol. 4, no. 1, pp. 217-234).

The first bacterins against *Leptospirosis* were developed more than one hundred years ago. As of today inactivated whole cell preparations remain the only licensed products for use in animal and human health. They elicit antibody responses against the major immunodominant bacterial antigen, the lipopolysaccharide (LPS). Its composition varies between serovars, hence a narrow-spectrum serogroup specific protective response. Humans, however, as well as animals—dogs in particular—are exposed to multiple serovars, with strong temporal and regional variations in the epidemiology. This is an important problem for the vaccine industry because there is a long and costly regional development by species and by geographic location.

Accordingly, there is an urgent need for an effective vaccine against broad range *Leptospira* spirochetes infection in canines and felines.

SUMMARY OF THE INVENTION

The invention provides a composition or vaccine that contains a live attenuated *Leptospira interrogans*. In particular, the present invention provides a recombinant or attenuated *Leptospira interrogans* that contains a mutated fliM gene that is non-functional. The fliM gene of the recombinant or attenuated *Leptospira interrogans* may be deleted. The fliM gene may encode a mutated fliM protein wherein the FliM protein is not translated or the C-terminal region of the fliM protein is deleted.

The present invention relates to an attenuated *Leptospira interrogans* strain. In particular, the invention provides the *Leptospira interrogans* strains under the CNCM deposit Nos. CNCM I-5132 and CNCM I-5133, or any descendant or progeny of the strains. The descendants or progenies of the deposited strains may have the entire fliM gene deleted.

The present invention showed surprising benefit of the vaccination using the live attenuated *Leptospira interrogans* vaccine to protect animals against homologous and heterologous *Leptospira* challenges. The present invention also demonstrated surprisingly that cross protection can only be achieved by using a virulence attenuated strain directly issued from a fully virulent isolate but not with an avirulent saprophytic strain.

BRIEF DESCRIPTION OF THE DRAWINGS

FIGS. 8A-8D depict the DNA and protein sequences and sequence alignments.

FIG. 9 is a table showing the SEQ ID NOs assigned to the DNA and protein sequences.

DETAILED DESCRIPTION OF THE INVENTION

Figure 1:
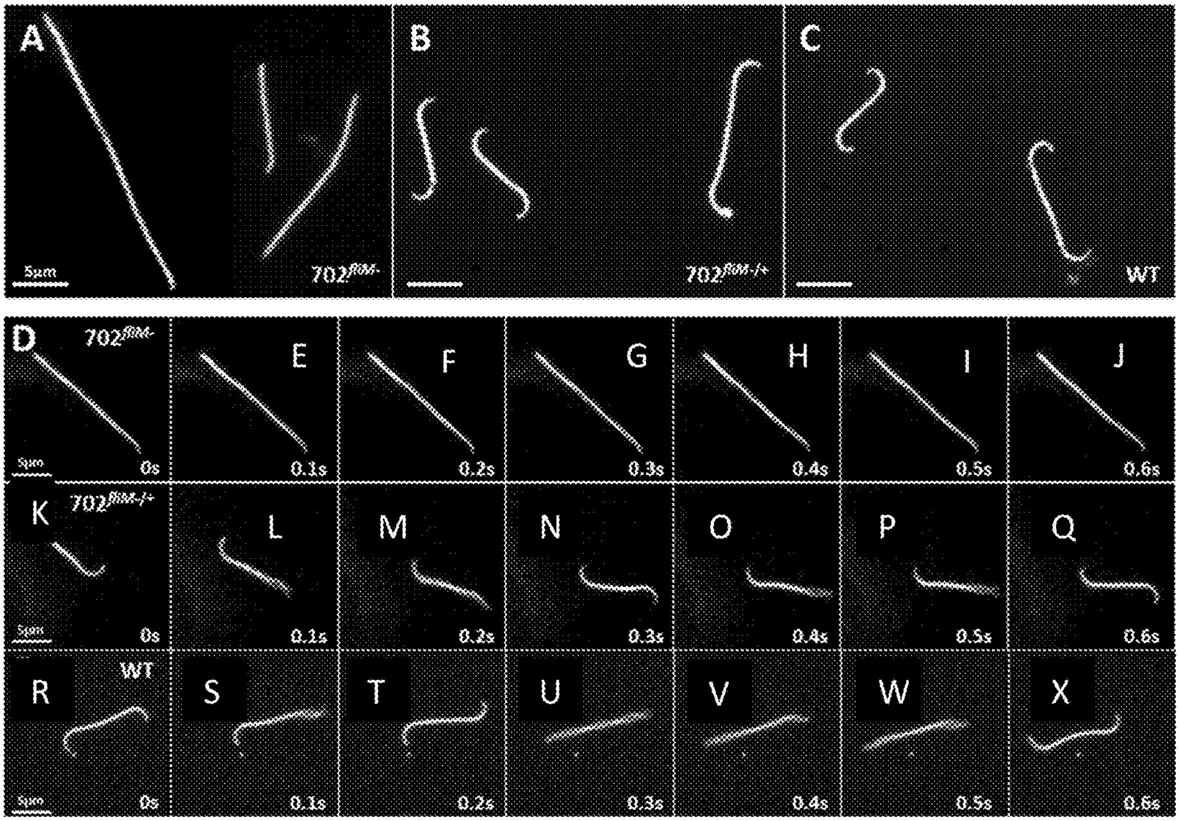
FIG. 1A is *L. interrrogans* serogroup autralis mutant strain $702^{fliM-}$.
FIG. 1B is *L. interrrogans* serogroup autralis mutant strain $702^{fliM-/+}$ restored with a functional fliM gene.
FIG. 1C is wild type *L. interrrogans* serogroup autralis strain.
FIG. 1D is *L. interrrogans* serogroup autralis mutant strain $702^{fliM-}$; time lapse at 0 s.
FIG. 1E is *L. interrrogans* serogroup autralis mutant strain $702^{fliM-}$; time lapse at 0.1 s.
FIG. 1F is *L. interrrogans* serogroup autralis mutant strain $702^{fliM-}$; time lapse at 0.2 s.
FIG. 1G is *L. interrrogans* serogroup autralis mutant strain $702^{fliM-}$; time lapse at 0.3 s.
FIG. 1H is *L. interrrogans* serogroup autralis mutant strain $702^{fliM-}$; time lapse at 0.4 s.
FIG. 1I is *L. interrrogans* serogroup autralis mutant strain $702^{fliM-}$; time lapse at 0.5 s.
FIG. 1J is *L. interrrogans* serogroup autralis mutant strain $702^{fliM-}$; time lapse at 0.6 s.
FIG. 1K is *L. interrrogans* serogroup autralis mutant $702^{fliM-/+}$ restored with a functional fliM gene; time lapse at 0 s.
FIG. 1L is *L. interrrogans* serogroup autralis mutant $702^{fliM-/+}$ restored with a functional fliM gene; time lapse at 0.1 s.
FIG. 1M is *L. interrrogans* serogroup autralis mutant $702^{fliM-/+}$ restored with a functional fliM gene; time lapse at 0.2 s.
FIG. 1N is *L. interrrogans* serogroup autralis mutant $702^{fliM-/+}$ restored with a functional fliM gene; time lapse at 0.3 s.
FIG. 1O is *L. interrrogans* serogroup autralis mutant $702^{fliM-/+}$ restored with a functional fliM gene; time lapse at 0.4 s.
FIG. 1P is *L. interrrogans* serogroup autralis mutant $702^{fliM-/+}$ restored with a functional fliM gene; time lapse at 0.5 s.
FIG. 1Q is *L. interrrogans* serogroup autralis mutant $702^{fliM-/+}$ restored with a functional fliM gene; time lapse at 0.6 s.
FIG. 1R is wild type *L. interrrogans* serogroup autralis strain; time lapse at 0 s.
FIG. 1S is wild type *L. interrrogans* serogroup autralis strain; time lapse at 0.1 s.
FIG. 1T is wild type *L. interrrogans* serogroup autralis strain; time lapse at 0.2 s.
FIG. 1U is wild type *L. interrrogans* serogroup autralis strain; time lapse at 0.3 s.
FIG. 1V is wild type *L. interrrogans* serogroup autralis strain; time lapse at 0.4 s.
FIG. 1W is wild type *L. interrrogans* serogroup autralis strain; time lapse at 0.5 s.
FIG. 1X is wild type *L. interrrogans* serogroup autralis strain; time lapse at 0.6 s.

It is noted that in this disclosure and particularly in the claims, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

The singular terms "a," "an," and "the" include plural referents unless context clearly indicates otherwise. Similarly, the word "or" is intended to include "and" unless the context clearly indicate otherwise. The word "or" means any one member of a particular list and also includes any combination of members of that list.

The term "animal" is used herein to include all mammals, birds and fish. The animal as used herein may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), bovine (e.g., cattle), swine (pig), ovine (e.g., sheep, goats, lamas, bisons), avian (e.g., chicken, duck, goose, turkey, quail, pheasant, parrot, finches, hawk, crow, ostrich, emu and cassowary), primate (e.g., prosimian, tarsier, monkey, gibbon, ape), humans, and fish. The term "animal" also includes an individual animal in all stages of development, including embryonic and fetal stages.

The term "nucleic acid", "nucleotide", and "polynucleotide" are used interchangeably and refer to RNA, DNA, cDNA, or cRNA and derivatives thereof, such as those containing modified backbones. It should be appreciated that the invention provides polynucleotides comprising sequences complementary to those described herein. The "polynucleotide" contemplated in the present invention includes both the forward strand (5' to 3') and reverse complementary strand (3' to 5'). Polynucleotides according to the invention can be prepared in different ways (e.g. by chemical synthesis, by gene cloning etc.) and can take various forms (e.g. linear or branched, single or double stranded, or a hybrid thereof, primers, probes etc.).

The term "genomic DNA", or "genome" is used interchangeably and refers to the heritable genetic information of a host organism. The genomic DNA comprises the DNA of the nucleus (also referred to as chromosomal DNA) but also the DNA of the plastids (e.g., chloroplasts) and other cellular organelles (e.g., mitochondria). The genomic DNA or genome contemplated in the present invention also refers to the RNA of a virus. The RNA may be a positive strand or a negative strand RNA. The term "genomic DNA" contemplated in the present invention includes the genomic DNA containing sequences complementary to those described herein. The term "genomic DNA" also refers to messenger RNA (mRNA), complementary DNA (cDNA), and complementary RNA (cRNA).

The term "gene" is used broadly to refer to any segment of polynucleotide associated with a biological function. Thus, genes or polynucleotides include introns and exons as in genomic sequence, or just the coding sequences as in cDNAs, such as an open reading frame (ORF), starting from the start codon (methionine codon) and ending with a termination signal (stop codon). Genes and polynucleotides can also include regions that regulate their expression, such as transcription initiation, translation and transcription termination. Thus, also included are promoters and ribosome binding regions (in general these regulatory elements lie approximately between 60 and 250 nucleotides upstream of the start codon of the coding sequence or gene; Doree S M et al.; Pandher K et al.; Chung J. Y et al.), transcription terminators (in general the terminator is located within approximately 50 nucleotides downstream of the stop codon of the coding sequence or gene; Ward C K et al.). Gene or polynucleotide also refers to a nucleic acid fragment that expresses mRNA or functional RNA, or encodes a specific protein, and which includes regulatory sequences.

The term "heterologous DNA" as used herein refers to the DNA derived from a different organism, such as a different cell type or a different species from the recipient. The term also refers to a DNA or fragment thereof on the same genome of the host DNA wherein the heterologous DNA is inserted into a region of the genome which is different from its original location.

As used herein, the term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

The terms "recombinant" and "genetically modified" are used interchangeably and refer to any modification, alteration or engineering of a polynucleotide or protein in its native form or structure, or any modification, alteration or engineering of a polynucleotide or protein in its native environment or surrounding. The modification, alteration or engineering of a polynucleotide or protein may include, but is not limited to, deletion of one or more nucleotides or amino acids, deletion of an entire gene, codon-optimization of a gene, conservative substitution of amino acids, insertion of one or more heterologous polynucleotides.

An "isolated" biological component (such as a nucleic acid or protein or organelle) refers to a component that has been substantially separated or purified away from other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

In one embodiment, the present invention provides a *L. interrogans* composition or vaccine comprising an attenuated or recombinant *L. interrogans* (LI) strain that contains a mutated flits (LIC11836) gene. The term "mutated flits gene" refers to the fliM gene of *L. interrogans* that is altered or engineered which results in a non-functional fliM protein upon expression. The alteration or engineering of the fliM gene includes mutation or deletion of a segment of the fliM gene which is essential for the expression of a functional fliM protein. The alteration or engineering of the fliM gene also includes mutation or deletion of one or more nucleotides which are essential for the expression of a functional fliM protein. The term "mutated flits gene" also includes deletion of the entire fliM gene of *L. interrogans* wherein fliM protein is not expressed.

The term "composition" comprises any vaccine or immunological composition, once it has been injected to a host, including canines, felines, equine and humans, that induces an immune response in the host, and/or protects the host from leukemia, and/or which may prevent implantation of the parasite, and/or which may prevent disease progression in infected subjects, and/or which may limit the diffusion of runaway parasites to internal organs. This may be accomplished upon vaccination according to the present invention through the induction of cytokine secretion, notably IFN-gamma secretion (as example of a method of measurement of IFN-gamma secretion, the Quantikine® immunoassay from R&D Systems Inc. (catalog number# CAIF00) could be used (Djoba Siawaya J F et al.)).

In another embodiment, the present invention provides an attenuated or recombinant *L. interrogans* wherein the gene in the native (wild-type) *L. interrogans* genome encoding the FliM protein is deleted. In yet another embodiment, the present invention provides an attenuated or recombinant *L. interrogans* wherein the fliM gene is mutated to produce one or more pre-mature stop codons within the gene. The term "fliM gene" includes any gene or polynucleotide that encodes the fliM of *L. interrogans*, and homologs, fragments or variants thereof. The flits gene may encode a fliM protein having at least 75%, 80%, 85%, 90%, 95%, 95%, 96%, 97%, 98%, 99%, 99.1%, 99.2%, 99.3%, 99.4%, 99.5%, 99.6%, 99.7%, 99.8% or 99.9% sequence identity to SEQ ID NO: 17, 18, 19 or 20, or a variant thereof. The fliM gene having at least 75%, 80%, 85%, 90%, 95%, 95%, 96%, 97%, 98%, 99%, 99.1%, 99.2%, 99.3%, 99.4%, 99.5%, 99.6%, 99.7%, 99.8% or 99.9% sequence identity to SEQ ID NO:17, 18, 19 or 20 is also encompassed in the present invention. In another aspect, the present invention provides a recombinant *L. interrogans* wherein the fliM gene in the native (wild-type) *L. interrogans* genome encoding the fliM protein is altered or engineered resulting in a mutated fliM protein.

In one embodiment, the invention provides *L. interrogans* strains under the CNCM deposit numbers CNCM I-5132 and CNCM I-5133, or any parent, descendant or progeny of the deposited strains.

In one embodiment, the composition or vaccine of the invention includes a live attenuated *L. interrogans* strain. The strains were deposited at CNCM (Collection Nationale de Cultures de Micro-organismes) on Sep. 1, 2016 in accordance with Budapest Treaty and were accorded Accession Nos. CNCM I-5132 and CNCM I-5133. In another embodiment, the present invention contemplates preparation and isolation of a progeny or descendant of a *L. interrogans* strain that has been deposited at CNCM under the Accession Numbers CNCM I-5132 and CNCM I-5133. The invention therefore extends to *L. interrogans* strains which are derived from the deposited strains through propagation or alteration in an identical or divergent form. The progenies or descendants of CNCM I-5132 and CNCM I-5133 strains include the *L. interrogans* strain wherein the fliM gene is deleted. The progenies or descendants may comprise a mutated fliM gene encoding an FliM protein having at least 75%, 80%, 85%, 90%, 95%, 95%, 96%, 97%, 98%, 99%, 99.1%, 99.2%, 99.3%, 99.4%, 99.5%, 99.6%, 99.7%, 99.8% or 99.9% sequence identity to the sequence as set forth in SEQ ID NO: 17, 18, 19 or 20. The progeny or descendant may comprise a polynucleotide having at least 75%, 80%, 85%, 90%, 95%, 95%, 96%, 97%, 98%, 99%, 99.1%, 99.2%, 99.3%, 99.4%, 99.5%, 99.6%, 99.7%, 99.8% or 99.9% sequence identity to the sequence as set forth in SEQ ID NO:13, 14, 15, or 16.

In one embodiment, the invention provides for the administration of a therapeutically effective amount of a vaccine or composition for the delivery an *L. interrogans* antigen in a target cell. Determination of the therapeutically effective amount is routine experimentation for one of ordinary skill in the art. In another embodiment, the vaccine or composition comprises an attenuated *L. interrogans* strain, and a pharmaceutically or veterinarily acceptable carrier, adjuvant, vehicle or excipient. In an embodiment, the pharmaceutically or veterinarily acceptable carrier, vehicle, adjuvant, or excipient facilitates transfection and/or improves preservation of the virus, bacterium or protein.

The pharmaceutically or veterinarily acceptable carriers, adjuvants, vehicles, or excipients are well known to the one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier, adjuvant, vehicle, or excipients that can be used for methods of this invention include, but are not limited to, poly-(L-glutamate) or polyvinylpyrrolidone. The pharmaceutically or veterinarily acceptable carrier, adjuvant, vehicle, or excipients may be any compound or combination of compounds facilitating the administration of the vector (or protein expressed from an inventive vector in vitro); the carrier, vehicle, adjuvant, or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The immunogenic compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman D. M. et al., Proc. Natl. Acad. Sci., USA, 1996, 93, 2879-2883; WO98/16247), (3) an oil in water emulsion, such as the SPT emulsion described on p 147 of "Vaccine Design, The Subunit and Adjuvant Approach" published by M. Powell, M. Newman, Plenum Press 1995, and the emulsion MF59 described on p 183 of the same work, (4) cation lipids containing a quaternary ammonium salt, (5) cytokines, (6) aluminum hydroxide or aluminum phosphate or (7) saponin, (8) Dimethyldioctadecyl ammonium bromide (Vaccine Design p. 157), (9) Aridine (Vaccine Design p. 148) other adjuvants discussed in any document cited and incorporated by reference into the instant application, or (8) any combinations or mixtures thereof.

The oil in water emulsion (3), can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters.

The oil is used in combination with emulsifiers to form an emulsion. The emulsifiers may be nonionic surfactants, such as: esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated, or polyoxypropylene-polyoxyethylene copolymer blocks, such as Pluronic, e.g., L121. Some of the emulsions, such as TS6, TS7, TS8 and TS9 emulsions, are described in U.S. Pat. Nos. 7,608,279 and 7,371,395.

The polymers of acrylic or methacrylic acid (1) are preferably crosslinked, in particular with polyalkenyl ethers of sugars or polyalcohols. These compounds are known under the term carbomer (Pharmeuropa vol. 8, No. 2, June 1996). Persons skilled in the art can also refer to U.S. Pat. No. 2,909,462 describing such acrylic polymers crosslinked with a polyhydroxylated compound having at least 3 hydroxyl groups, preferably not more than 8, the hydrogen atoms of at least three hydroxyls being replaced with unsaturated aliphatic radicals having at least 2 carbon atoms. The preferred radicals are those containing 2 to 4 carbon atoms, e.g. vinyls, allyls and other ethylenically unsaturated groups. The unsaturated radicals may themselves contain other substituents, such as methyl. The products sold under the name CARBOPOL™ (BF Goodrich, Ohio, USA) are particularly appropriate. They are crosslinked with an allyl sucrose or with allylpentaerythritol. Among them, there may be mentioned CARBOPOL™ 974P, 934P and 971 P.

Among the copolymers of maleic anhydride and of alkenyl derivative, the EMA™ copolymers (Monsanto) which are copolymers of maleic anhydride and of ethylene, which are linear or crosslinked, for example crosslinked with divinyl ether, are preferred.

The proportions of adjuvant which are useful are well known and readily available to the one skilled in the art. By way of example, the concentration of polymers of acrylic or methacrylic acid or of anhydride maleic and alkenyl copolymers in the final vaccine composition will be from 0.01% to 1.5% W/V, more particularly from 0.05 to 1% W/V, preferably from 0.1 to 0.4% W/V.

In one embodiment, the adjuvant may include TS6 (U.S. Pat. No. 7,371,395), LR2, LR3 and LR4 (U.S. Pat. No. 7,691,368), TSAP (US20110129494), TRIGEN™ (Newport Labs), synthetic dsRNAs (e.g. poly-IC, poly-ICLC [HILTONOL®]), and MONTANIDE™ adjuvants (W/O, W/O/W, O/W, IMS and Gel; all produced by SEPPIC).

In yet another embodiment, the adjuvant may include interleukin-2 (IL-2), IL-12, interferon α (IFNα), polyinosinic and polycytidylic acid, and cytidine-phosphate-guanosine oligodeoxynucleotides (CpG ODN), which are known to significantly enhance CMI response to CIV vaccines (Vet. Immuno. and Immunopath. Vol. 129, Issues 1-2, 15 May 2009, *Pages* 1-13).

In a specific embodiment, the pharmaceutical composition is directly administered in vivo. Advantageously, the pharmaceutical and/or therapeutic compositions and/or formulations according to the invention comprise or consist essentially of or consist of an effective quantity to elicit a therapeutic response of one or more expression vectors and/or polypeptides as discussed herein; and, an effective quantity can be determined from this disclosure, including the documents incorporated herein, and the knowledge in the art, without undue experimentation.

The composition or vaccine may contain a dose from about $10^2$ to about $10^{20}$, about $10^3$ to about $10^{18}$, about $10^4$ to about $10^{16}$, about $10^5$ to about $10^{12}$ VLPs (virus like particles) produced in vitro or in vivo from a viral vector, a plasmid, or baculovirus. The viral vector may be titrated based on any virus titration methods including, but not limited to, FFA (Focus Forming Assay) or FFU (Focus Forming Unit), $TCID_{50}$ (50% Tissue Culture Infective Dose), PFU (Plaque Forming Units), and $FAID_{50}$ (50% Fluorescent Antibody Infectious Dose), and the VLPs produced in vitro can be titrated by hemagglutination assay, ELISA, and electron microscopy. Other methods may also be applicable depending on the type of VLP.

The composition or vaccine may contain from about $10^{2.0}$ to about $10^{10.0}$ bacterial counts (for example, number of leptpspires)/dose. The composition or vaccine may contain equivalent bacterial counts in the case of inactivated/killed composition or vaccine. The dose volumes can be between about 0.1 and about 10 ml, between about 0.2 and about 5 ml. By definition, the volume of one dose means the total volume of vaccine administered at once to one animal.

The present invention contemplates at least one administration to an animal of an efficient amount of the therapeutic composition made according to the invention. The animal may be male, female, pregnant female and newborn. This administration may be via various routes including, but not limited to, intramuscular (IM), intradermal (ID) or subcutaneous (SC) injection or via intranasal or oral administration. The therapeutic composition according to the invention can also be administered by a needleless apparatus (as, for example with a Pigjet, Biojector or Vitajet apparatus (Bioject, Oreg., USA)).

The composition or vaccine is administered to a dog or a cat. A booster administration can be done if necessary around 2 to 11 weeks after the first administration.

Liquid jet needle-free injectors are devices performing injections of a certain amount of liquid under high pressure through a minute orifice. In an embodiment, the needle-free injection is a DERMA-VAC NF transdermal vaccinator system.

Optionally, the administration can be repeated, as booster administration, at suitable intervals if necessary or desirable, e.g. from about 2 to about 11 weeks after the first administration. A booster administration can also be repeated every 6 months or every year.

In one embodiment of the invention, a prime-boost regimen can be employed, which is comprised of at least one primary administration and at least one booster administration using at least one common polypeptide, antigen, epitope or immunogen. Typically the same composition or vaccine is used as the primary administration and the boost. This administration protocol is called "prime-boost". However, different compositions or vaccines may be used as the prime administration and the boost.

Another object is a vaccination kit or set, comprising at least one vaccine vial containing the vaccine of the present invention, and operatively assembled to perform the administration of the vaccine to an animal of the canine family. Such vaccination kit or set is able to elicit a safe and protective immune response against influenza infection.

The invention will now be further described by way of the following non-limiting examples.

EXAMPLES

Construction of DNA inserts, plasmids and recombinant viral vectors was carried out using the standard molecular biology techniques described by J. Sambrook et al. (Molecular Cloning: A Laboratory Manual, 4th edition, Cold Spring Harbor Laboratory, Cold Spring Harbor, N.Y., 2014).

Example 1 Isolation and Identification of *L. interrogans* Mutant and Vaccination Study in Hamsters Against Homologous and Heterologous Challenge Introduction Pathogenic *Leptospira* are highly invasive spirochetes responsible for leptospirosis, the most widespread zoonosis worldwide. Symptoms vary from chronical infection to multiple organ failure with a significant mortality rate. Virulence factors are not well known due to a lack of adequate and efficient genetic tools for these slow-growing bacteria. Among identified pathogenic determinants, motility is reported as critical as it may participate in pathogen entry and dissemination in the host. However, direct link between motility and virulence has not been demonstrated yet in *Leptospira*. In this study, we isolated a mutated *L. interrogans* strain lacking both motility and virulence. Whole genome sequencing allowed to identify a single deletion in fliM gene disrupting the whole protein. FliM is annotated as a flagellar motor switch protein and a component of the C-ring, a central unit of flagellar motor regulating its rotation direction. In this study, we confirmed the implication of fliM in flagellar rotation and assembly. Flagella were indeed either absent from the cell or present at one or both extremities in a truncated form, and rotation movements of cell extremities were lacking. Shorter and non-functional flagella induced loss of translational and non-translational motility as well as morphological defects: hook and spiral shaped-ends were lacking and long chains of bacteria were observed, indicating division defects. In addition, our strain failed to induce an infection on hamster model even at high infectious dose ($10^8$ bacteria). Genetic complementation in trans with a replicative plasmid restored wild type morphology, flagellar length and rotation, motility and infectivity. We therefore confirmed the function of FliM in *Leptospira* as fundamental for flagellar structure and rotation, both required for translational motility. Besides, we validate that absence of motility is directly correlated to lack of infectivity, proving that motility is essential for virulence.

Strains

*Leptospira interrogans* serogroup *Australis* strains $702^{fliM-}$, $702^{fliM-/+}$ 733 and 732, further designed as Wild-Type (WT), *L. interrogans* serogroup Icterohaemorrhagiae and *L. biflexa* serovar Patoc were grown at 29° C. in liquid Ellinghausen-McCullough-Johnson-Harris with shaking or on EMJH agar plates (Difco). *Leptospira* strains were identified at the species (16S rRNA), serogroup (MAT with rabbit antisera) and genotype (MLVA) levels. When needed, spectinomycin was added to cultures to a final concentration of 50 μg/ml. The strains $702^{fliM-}$ and $702^{fliM-/+}$ 733 were deposited at CNCM (Collection Nationale de Cultures de Micro-organismes) on Sep. 1, 2016 and accorded Accession Nos. CNCM I-5132 and CNCM I-5133, respectively.

Genomics

DNA was extracted with QiaAmp DNA Blood Midi kit (Qiagen) for whole genome sequencing and with QiaAmp DNA Mini kit (Qiagen) for PCR amplifications, according to manufacturer's protocols. The genome sequences of WT and $702^{flM}$ strains were determined. Sequencing reads were assembled using CLC Genomics Workbench 7 (CLCbio) and annotated with Glimmer logarithm from GenostarSuite 4 (Genostar, Montbonnot Saint Martin, France). Polymorphisms between these two strains were detected and analyzed with Genostar Suite 4 and validated by mapping sequencing reads on identified regions with CLC Genomics Workbench 7.

PCR

PCR was performed on 1 ng to 10 ng of template DNA with IU of Phusion High-fidelity DNA polymerase (Thermo), 1× Phusion Buffer, 200 μM of each dNTP (Life), 0.5 μM of each primer in 50 μl of water, on Biometra TGradient thermocycler. Primers used for this study are listed in Table 1.

TABLE 1

Primer sequences

| Primer | Fw/Rv | Amplification | Sequence |
|---|---|---|---|
| PflgA | Fw | fusion FlgB-fliM | TAATACCCGAGCTTCAAGGAAG |
| FliMR2 | Rv | fusion FlgB-fliM | TAACTTCAATTCTAATATTCTTGTTCAGAACG |

TABLE 1-continued

| Primer sequences | | | |
|---|---|---|---|
| Primer | Fw/Rv | Amplification | Sequence |
| CF109 | Fw | fliM-external primers | CAATCGTGCTGAAGAATCTGAAAGAG |
| CF099 | Rv | fliM-external primers | CTGTAGCACAAGCCTGATTCGC |
| CF108 | Fw | fli-internal primers | TCCCAAGATGAAATTGACGCG |
| CF103 | Rv | fliM-internal primers | CTACTCTTTCACCGATCTGAATGGC |
| flaB4F | Fw | qRT-PCR flaB4 | CTCATATTTGCTTGTGCGAGC |
| flaB4R | Rv | qRT-PCR flaB4 | GAACGCTACTGGTTTACAATTAGTTGC |
| rpoBF | Fw | qRT-PCR rpoB | ATGGAGCGGAACGTGTAGTC |
| rpoBR | Rv | qRT-PCR rpoB | CTTCGTTCGTTCCATGTCCT |

The sequence identification numbers are as follows: SEQ ID NO:1=PflgA, SEQ ID NO. 2=FliMR2, SEQ ID NO:3=CF109, SEQ ID NO:4=CF099, SEQ ID NO:5=CF108, SEQ ID NO:6=CF103, SEQ ID NO:7=flaB4F, SEQ ID NO:8=flaB4R. SEQ ID NO:9=rpoBF, SEQ ID NO:10=rpoBR.

Genetic Complementation

The coding sequence of fliM (LIC11836) was amplified from genomic DNA of *L. interrogans* serovar Manilae strain L495 (100% sequence identity with FliM of *Australis* strains at the amino acid level) using primers FlimF (5'-CGACA CATATGACAGAAATITTAT-3'; SEQ ID NO:11) and FlimR2 (5'-TAACTTCAATTCTAATAT-TCTTGTTCAGAACG-3'; SEQ ID NO:12), which incorporated a restriction digestion site for NdeI (underlined bases), and cloned into PCRII-TOPO vector (Invitrogen) according to manufacturer's instructions. The fliM coding sequence was then digested with NdeI and XhoHI, purified, and inserted into the same restriction sites of pCRPromFlgB to generate a transcriptional fusion between the gene and the *Borrelia burgdorferi* flgB promoter. The DNA fragment containing the transcriptional fusion was released by EcoRI digestion and cloned into the corresponding site of the replicative plasmid pMaORI (Pappas C J et al., 2015, Appl. Environ. Microbiol., February 2015), to generate pCF036. The fliM complementation construct was introduced in strain 702 by conjugation with *E. coli* β2163 carrying pCF036 as previously described (Pappas C J et al., 2015, supra; Lambert A et al., 2014, FEMS Microbiol. *Lett., p. fnu*054). Plates were incubated 5 weeks to obtain the complemented strain $702^{fliM-/+}$.

Soft Agar Plate Assay

Motility of *Leptospira* strains was evaluated onto 0.5% and 0.3% agar EMJH plates by inoculating 5 μl of mid-log phase cultures ($OD_{450nm}$ of approximately 0.3). Plates were incubated at 29° C. and daily observed. Briefly, soft EMJH plates with 0.5% agar inoculated with $702^{filM-}$, $702^{filM-/+}$ and WT were observed after 10 days of incubation. $702^{filM-}$ didn't spread from its inoculation point (FIG. 2A), contrary to $702^{filM-/+}$ (FIG. 2B) and WT (FIG. 2C) which formed a circle of 2.6 cm and 2.2 cm respectively. One representative plate of three experiments is shown. Identical results were obtained on three 0.3% agar plates.

Dark Field Microscopy

Leptospires were observed by dark-field microscopy using ×20 to ×200 magnification with Olympus BX-53 139 microscope coupled with a camera Hamamatsu Orca Flash2.8. See FIGS. 1A-1X. Pictures were taken with CellSense Software (Olympus) and videos were recorded with MicroManager 1.4 software (μManager). Images were post-treated with ImageJ software (ImageJ), and three pictures of each strain containing approximately 80 bacteria were used to manually measure bacterial length with ImageJ.

Transmission Electron Microscopy (TEM)

Commercial 400 mesh carbon-coated copper grids were glow-discharged just before use. Samples were placed in contact with the grids for 10 min. Grids with samples were then fixed with 2% glutaraldehyde in 0.1M cacodylate sodium buffer for 10 min and washed 3 times for 1 min in water for biosecurity requirement. Grids were dried and negatively stained with 4% uranyl acetate for few seconds. Samples were observed with a transmission electron microscope (TEM) TECNAI T12 FEI operating at 120 kV. For manual length measurements of flagella, 5 fields were chosen randomly and analyzed using ImageJ software.

Recombinant FliM Purification and Antisera Production

The plasmid containing flgB-fliM fusion was digested by NdeI and BamHI and cloned into corresponding sites in pET28 vector (EMD Biosciences). The resulting plasmid pET28-(His)6FliM was introduced into *E. coli* BL21DE3 cells. Recombinant protein expression was induced on 2 L of transformed cells at $OD_{600\ nm}$=0.7 by addition of 1 mM Isopropyl β-D-1-thiogalactopyranoside (IPTG) for 4 h at 37° C. FliM was highly insoluble in the growth condition used and was purified from inclusion bodies by the following manner. Cells were harvested and pellets were resuspended in buffer A (50 mM NaH2PO4 pH 8.0, 300 mM NaCl, 10 mM Imidazole, 10% glycerol) and lysed by sonication in the presence of protease inhibitor cocktail (complete mini EDTA-free, Roche) and 1 mM phenylmetylsulfonyl fluoride (PMSF). The insoluble fraction obtained after a 60 min centrifugation at 40,000×g at 4° C. was resuspended in buffer A containing 1% Triton X100 to solubilize membrane proteins. Inclusion bodies obtained after a 30 min centrifugation at 40,000×g were solubilized in buffer B (100 mM NaH2PO4 pH 8.0, 8M urea, 10 mM Tris pH 8.0, 200 mM NaCl, 1 mM PMSF, 0.1% Triton X100), incubated for 1 h at room temperature with stirring and centrifuged 30 min at 4° C. at 40,000×g. The supernatant was loaded on a nickel-nitrilotriacetic (Ni-NTA) resin (Qiagen) equilibrated with buffer B. Since recombinant (His)6-FliM could not be eluated from the column by conventional methods, the flow-through was used to further purify the protein by filtration on a 100 kDa cut-off cellulose membrane (Amicon Ultra 100K, Merck Millipores). The flow-through after filtration was dialyzed against C (50 mM Tris pH 8.0, 150 mM NaCl, 2 mM 2M urea, 2 mM DTT, 5 mM EDTA) and concentrated to 2.5 mg/mL.

To produce polyclonal sera, two rabbits were immunized 4 times with 2 mg of purified FliM protein, and sera were collected on day 38 (Aldevron).

Preparation of Periplasmic Flagella

Flagella extraction protocol was adapted from Lambert (2012, supra). Three independent mid-log phase cultures at $OD_{450\ nm}$ of approximately 0.3 ($5\times10^8$ cells/nil) of 200 ml for each strain were centrifuged at 8000×g 20 min at 4° C. Pellets were washed with 22 ml PBS and then with 24 ml sucrose solution (0.5 M sucrose, 0.15 M Tris pH 8). Cells were resuspended in 12 ml sucrose solution and stirred on ice for 10 min. Addition of 1.2 ml of 10% Triton X-1000 was followed by incubation of 30 min at room temperature. 120 µl of 10 mg/ml lysozyme were added dropwise and incubated 5 min on ice. Then 1.2 ml of 20 mM EDTA pH8 were added dropwise. After incubation of 2 h at room temperature, 2400 of 0.1M $MgSO_4$ were added and stirred 5 min at room temperature, then 240 µl of 0.1M EDTA were added and stirred again 5 min at room temperature. Mixtures were then centrifuged at 17000×g 15 min at 4° C. Supernatants were mixed with 1.6 ml 20% polyethylene glycol 8000 previously dissolved in 1M NaCl, and incubated 30 min on ice. Suspensions were centrifuged again at 24400×g for 45 min at 4° C. Pellets were resuspended in 2.5 ml of water and 100 µl of 1% sodium azide in PBS, and were placed at 4° C. overnight. Mixtures were then ultracentrifuged 45 min at 80 000×g at 4° C. in a Beckman Optima MAX Ultracentrifuge, with rotor TLA 100.3. Flagellar preparations were resuspended in an appropriate volume of water depending on the OD of the culture (approximately 800 µl) and 100 µl of 1% sodium azide.

Protein Gels

Cultures of leptospires were centrifuged for 10 min at 7000×g, washed once in PBS and then normalized in PBS at 1 or 5 $OD_{450\ nm}$ unit per milliliter to obtain whole cell lysates. These cell lysates and flagellar preparations were mixed with 3× lysis buffer composed of 0.2M Tris pH8, 16% 2-mercaptoethanol, 6% SDS, 30% glycerol and 0.06% bromophenol blue, and boiled at 100° C. for 10 min before loading on 4-20% TGX gels (SDS-PAGE, Biorad). 5 µl of ladders, Precision Plus All Blue Standards (Biorad) and Magic Mark XP (Life) and different volumes of samples were separated under 150V to 200V for 30 min to 1 h. Coomassie gels were washed 3 times with distilled water for 5 min, stained for 1 h with Simply Blue stain (Invitrogen) and destained in water bath for 1 h. Western Blots were performed by transferring proteins from gels to nitrocellulose membranes for 7 min at 25V and 1.3 mA per gel using Transblot-Turbo transfer system (Biorad). A specific sites on membranes were blocked after an incubation of 1 h in Odyssey buffer (Li-Cor). Rabbit primary antibodies anti-FlaB (LIC11531, 1:1000), FlaA2 (1:1000), FliM (1:100), LipL41 (1:100) were diluted in Odyssey buffer and incubated for 1 h. Membranes were then washed 3 times with PBS+0.1% Tween, and incubated with secondary anti-rabbit IgG (H&L) goat antibody IRdye800® Conjugated (Rockland) diluted 1:10000 for 45 min in the dark. Three more washes with PBS+0.1% Tween were performed before revelation using Odyssey® imaging system at 800 nm. Relative approximate quantification was performed by measuring intensities of bands with Odyssey® software (Li-Cor).

Immunofluorescence (IFA)

Protocol was adapted from Pinne and Haake (Pinne M et al., 2011, *J. Vis. Exp.*, no. 53). $5\times10^8$ leptospira were washed in PBS+5 mM $MgCl_2$ and then applied to a well of a 4 well Lab-Tek® II $CC^2$ Slide (Nunc). Cells adhesion was realized by incubating leptospires for 1 h at 29° C. Liquid was removed by gentle aspiration, and cells were fixed and permeabilized with 1 ml ice-cold 100% methanol for 20 min at −20° C. Non-specific sites were blocked with 1 ml of PBS-BSA 2% for 1 h. Leptospires were then incubated with 2041 of primary FlaB antibody diluted at 1:100 in PBS-BSA 2% for 1 h, then washed 3 times with 1 ml of PBS. Secondary antibody Cy™3-conjugated AffiniPure Goat Anti-Rabbit IgG (H+L, Jackson ImmunoResearch) diluted 1:100 in PBS-BSA 2% was added and incubated for 1 h. Cells were washed twice with 1 ml PBS and once with 1 ml of water. Chambers were removed and slides were air-dried for several minutes. A drop of ProLong® Gold Antifade reagent containing 4',6'-diamidino-2-phenylindole (DAPI) for DNA counterstaining (Life Technologies) and a coverslip were added, and incubated overnight in the dark. Slides were observed with a Nikon Eclipse Ti-S fluorescence microscope (Nikon) coupled to Digital Sigth DS-5Mc camera (Nikon) and pictures were acquired with Nikon NIS Elements F Package 4.0 (Nikon) and post-treated with ImageJ software.

Virulence Assay

Syrian Gold female hamsters of 6 to 7 weeks old were infected with $10^8$ *Leptospira* injected intraperitoneally. Duration of the study was first established at 21 days but protocol was stopped at day 14 given the rapid death of hamsters (see results section). 2 groups of 5 hamsters were infected by $702^{fliM-}$ and WT and 1 group of 10 hamsters was infected with $702^{fliM-/+}$ (see FIG. 6).

Protection Studies

Groups of twenty 4-week-old Syrian Gold female hamsters were vaccinated by intraperitoneal route (IP) with a single dose of $10^6$ live *L. interrogans* serogroup *Australis* $702^{fliM-}$ or $10^8$ live saprophytic *L. biflexa* serovar Patoc. As a control, a group of 10 hamsters was vaccinated with 1 ml of EMJH. Fourteen days after immunization, animals were challenged via the IP route with virulent *L. interrogans*. Half of the group received 20 leptospires of serogroup *Australis* strain 732 while the other half was inoculated with 1000 leptospires of Icterohaemorrhagiae. These challenge doses have been previously determined as the minimal amount of bacteria necessary to kill at least 80% of hamsters. Animals were monitored for 21 days after infection. Moribund hamsters were euthanized by intracardiac injection of Dolethal. See FIG. 7.

Accession Numbers

The genome sequences of *L. interrogans* strains 702 and 733 are available in GenBank under accession numbers NZ_LMXF00000000.1 and NZ_LMXK00000000.1, respectively.

Results

Isolation of a Spontaneous Nonmotile Mutant

*L. interrogans* serogroup *Australis* strain 702 was isolated from the blood of a dog with acute leptospirosis. The dog died from its infection a few days after sampling. The positive culture was apparently clonal with non-translating leptopires under dark-field microscopy. Similarly, after plating the isolate onto solid EMJH media, all colonies were small. Assuming that this non-motile phenotype arose from a motile parental strain, the closest phylogenetic strain was selected from the collection for further phenotypic analysis.

The motile strain 733, which was also isolated from a sick dog visiting the same clinics 3 months later, exhibited the same molecular (16S rRNA and MLVA profiles) and serological (serogroup *Australis*) features as the nonmotile strain 702. Furthermore, 702 and 733 showed similar cell growth kinetics (not shown). Taken together, these data indicate that the two strains are very close, thus strain 733 could be considered as a WT strain to be compared with 702 for following experiments. Strain 733 was consequently named WT.

Figure 2:
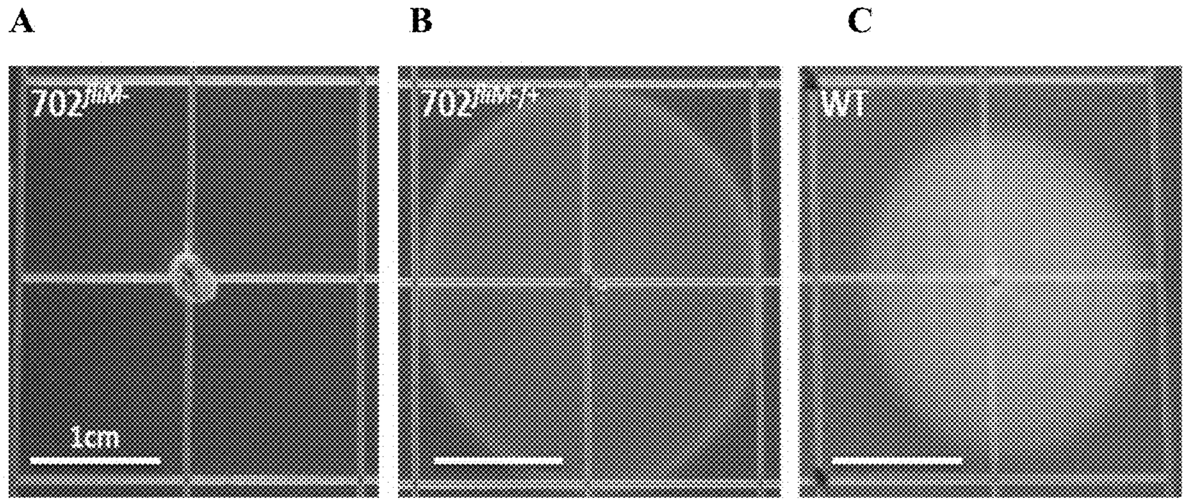
FIG. 2A is *L. interrrogans* serogroup autralis mutant strain $702^{fliM-}$ motility after 10 days of incubation.
FIG. 2B is *L. interrrogans* serogroup autralis mutant strain $702^{fliM-/+}$ restored with a functional fliM gene motility after 10 days of incubation.
FIG. 2C is wild type *L. interrrogans* serogroup autralis strain motility after 10 days of incubation.

Strain 702 presented an atypical straight morphology under dark field microscope, lacking characteristic hook and spiral-shaped extremities and missing translational and non-translational motility (FIGS. 1A and 1D-1J). Approximately 2% of total population showed a small hook on one extremity, conferring sporadic and slow rotational movements but unable to propel the cells. We confirmed this absence of motility of 702 on soft agar plates, as the strain didn't spread from its inoculation site contrary to WT (FIG. 2A). In addition, this strain showed a filamentous morphology. We measured cells length and compared to WT using different pictures at ×20 magnification. Average length of WT was 9.4 μm as already described for typical pathogenic *Leptospira* and 16.5 μm for 702 (on 275 counted bacteria). Moreover, distribution of cell sizes were different between the two strains: for WT, 99% of bacteria were shorter that 15 μm, and 1% comprised between 15 μm and 30 μm, whereas for the non-motile strain, 51% of bacteria were shorter than 15 μm, 43% between 15 μm and 30 μm, and 6% longer than 30 μm, including 2 bacteria of 70 μm, indicating probably division defects.

Figure 3:
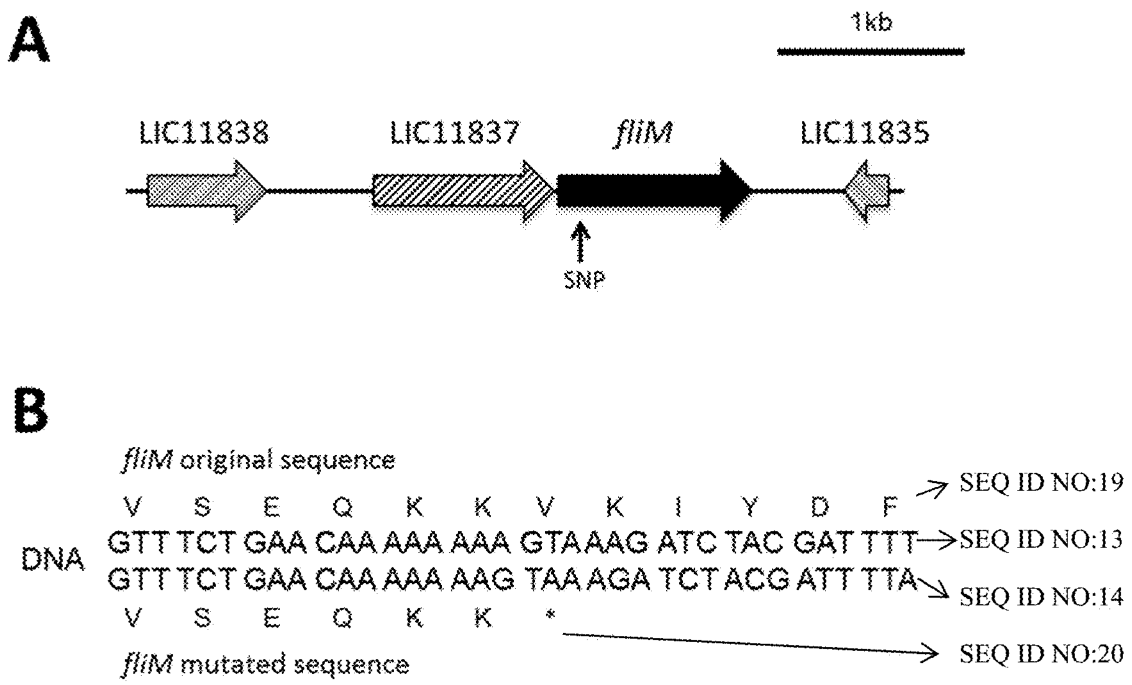
FIG. 3A is a diagram showing the location of the SNP of the *L. interrrogans* serogroup autralis mutant strain $702^{fliM-}$.
FIG. 3B is a diagram comparing the nucleotide sequences of wild type *L. interrrogans* serogroup autralis strain with the *L. interrrogans* serogroup autralis mutant strain $702^{fliM-}$.
Figure 4:
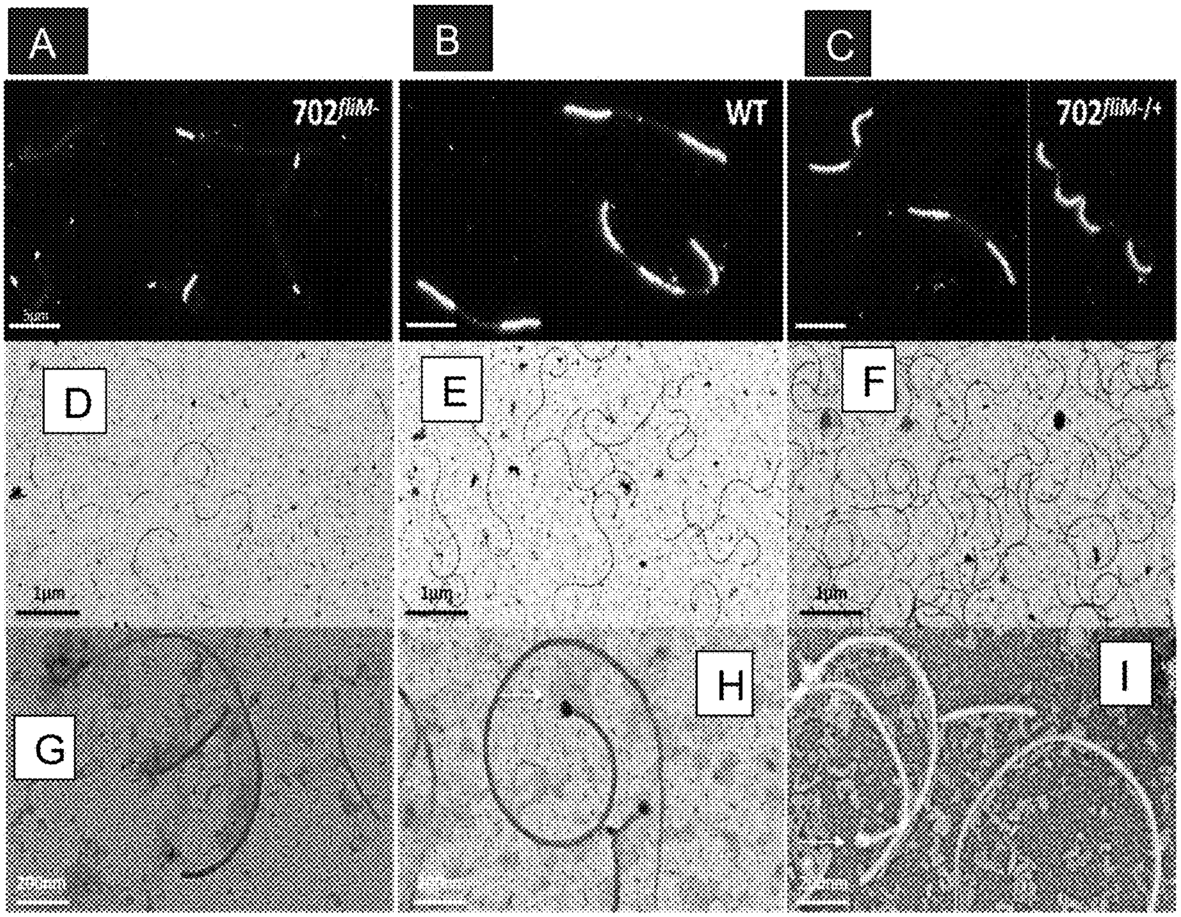
FIG. 4A is a FlaB immunofluorescence assay of *L. interrrogans* serogroup autralis mutant strain $702^{fliM-}$.
FIG. 4B is a FlaB immunofluorescence assay of *L. interrrogans* serogroup autralis mutant strain $702^{fliM-/+}$.
FIG. 4C is a FlaB immunofluorescence assay of wild type *L. interrrogans* serogroup autralis strain.
FIG. 4D is a flagella preparation after uranyl acetate staining of *L. interrrogans* serogroup autralis mutant $702^{fliM-}$.
FIG. 4E is a flagella preparation after uranyl acetate staining of *L. interrrogans* serogroup autralis mutant $702^{fliM-/+}$.
FIG. 4F is a flagella preparation after uranyl acetate staining of wild type *L. interrrogans* serogroup autralis strain.
FIG. 4G is a flagella preparation after uranyl acetate staining of *L. interrrogans* serogroup autralis mutant strain $702^{fliM-}$, higher magnification than 5D.
FIG. 4H is a flagella preparation after uranyl acetate staining of *L. interrrogans* serogroup autralis mutant strain $702^{fliM-/+}$, higher magnification than 5E.
FIG. 4I is a flagella preparation after uranyl acetate staining of wild type *L. interrrogans* serogroup autralis strain, higher magnification than 5F.
Figure 5:
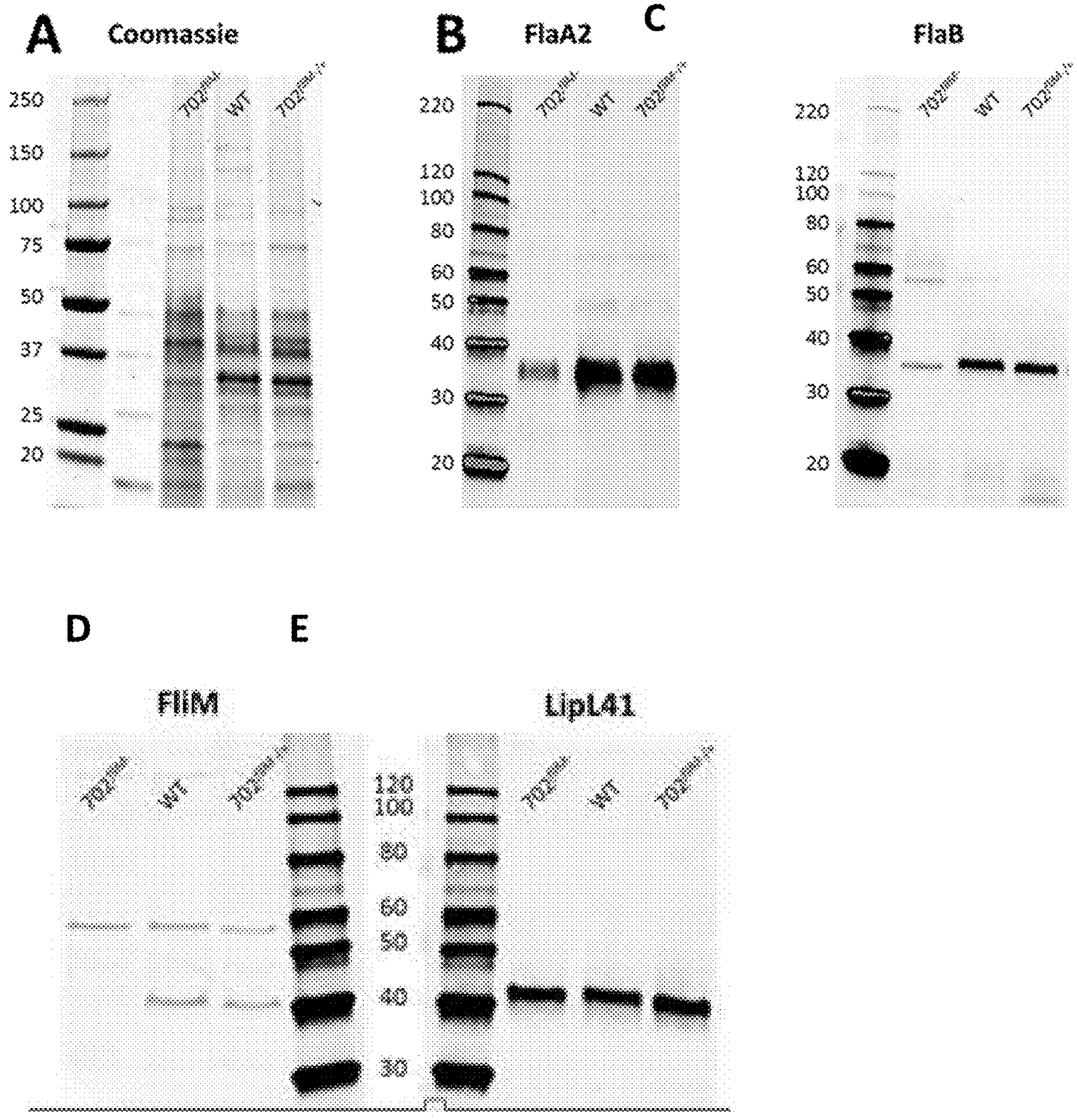
FIG. 5A is a coomassie stain of purified flagellar proteins from *L. interrrogans* serogroup autralis mutant strain $702^{fliM-}$, *L. interrogans* serogroup autralis mutant strain $702^{fliM-/+}$ and wild type *L. interrrogans* serogroup autralis strain.
FIG. 5B is a western blot using FlaA2 antibody of purified flagellar proteins from *L. interrrogans* serogroup autralis mutant strain $702^{fliM-}$, *L. interrrogans* serogroup autralis mutant strain $702^{fliM-/+}$ and wild type *L. interrrogans* serogroup autralis strain
FIG. 5C is a western blot using FlaB antibody of purified flagellar proteins from *L. interrrogans* serogroup autralis mutant strain $702^{fliM-}$, *L. interrrogans* serogroup autralis mutant strain $702^{fliM-/+}$ and wild type *L. interrrogans* serogroup autralis strain.
FIG. 5D is a western blot using FliM antibody of whole cell lysate from *L. interrrogans* serogroup autralis mutant strain $702^{fliM-}$, *L. interrrogans* serogroup autralis mutant strain $702^{fliM-/+}$ and wild type *L. interrrogans* serogroup autralis strain.
FIG. 5E is a western blot using LipL41 antibody of whole cell lysate from *L. interrrogans* serogroup autralis mutant strain $702^{fliM-}$, *L. interrrogans* serogroup autralis mutant strain $702^{fliM-/+}$ and wild type *L. interrrogans* serogroup autralis strain. This blot was performed for protein expression normalization.

A Single Spontaneous Mutation Abolished FliM Protein Expression in the Non-Motile Strain The whole genome of strains 702 and WT were sequenced to identify mutation(s) that could result in the motility-deficient phenotype in strain 702. 50,272,184 reads and 10,974,264 reads were analyzed for strains 702 and WT, respectively, representing a depth of coverage of 1000× and 200× respectively. Reads were assembled into contigs and annotated. Comparative analysis of the genome sequences led to the identification of two polymorphisms, one DIP and one nonsense SNP. These two mutations induced premature stop codon apparition on fliM (LIC11836) and LIC10453 genes. However, LIC10453 which encodes a hypothetical protein was also truncated 50 amino acids (on a total size of 364aa) downstream in two other motile *L. interrogans* strains available at MERIAL, suggesting that this gene is not essential to motility. By contrast, fliM, annotated as a flagellar motor switch protein, was found to be highly conserved among *Leptospira* genus, with more than 99% identity amongst pathogenic *L. interrogans* and *L. borgpetersenii* and 88% identity with the saprophytic *L. biflexa*. See FIG. 3B, fliM original sequence (GTT TCT GAA CAA AAA AAA GTA AAG ATC TAC GAT TIT; SEQ ID NO:13). This premature stop codon in fliM, which is the results of a 1-nucleotide deletion 105 bp downstream the start codon, was then more likely implied in the motility-deficient phenotype. See FIG. 3B, filM mutated sequence (GTT TCT GAA CAA AAA AAG <u>TAA</u> AGA TCT ACG ATT TTA; SEQ ID NO:14). This deletion was confirmed by PCR sequencing after amplification with primers CF109 (SEQ ID NO:3)-CF099 (SEQ ID NO:4) No polar effect due to this mutation is to be expected because no genes were present downstream of fliM (FIG. 3A). To further investigate the expression of FliM, we produced polyclonal antibodies to recombinant FliM. As expected, no FliM expression was detected in whole cell lysates of strain 702 (FIG. 5D). Mutation of fliM therefore caused absence of FliM expression and was likely responsible for loss of motility. We therefore further named this strain $702^{fliM-}$.

Complementation with fliM Restores Typical Cell Shape, Motility, and Virulence

To confirm that a mutation in fliM specifically causes loss of motility, we complemented the strain $702^{fliM-}$ in trans with the replicative vector pMaORI containing a functional fliM gene under the control of a constitutive promoter (fliM is the second gene of a putative operon FIG. 3A), preventing complementation with native fliM promoter). FliM expression was restored in the complemented strain to WT level according to Western Blot experiments on 3 independent cultures of $702^{fliM-/+}$ (FIG. 5D). Microscopic observations showed the restoration of wild type motility and morphology with hook and spiral-ends (FIGS. 1B and 1K-1Q). Spread of bacteria on soft agar plate was similar to WT (FIG. 2B). Moreover, no long filaments were observed and cell length was comparable to WT: on 275 measured bacteria, average length was 10.9 μm, including 91% shorter than 15 μm and 9% between 15 μm and 30 μm. Growth kinetics were similar to $702^{filM-}$ and WT. Taken together, these data prove that trans complementation successfully reintroduced functional fliM in strain $702^{filM-}$, and that fliM is essential for cell shapes, motility, and virulence.

filM Disruption Induces a Defect in Flagella Assembly

Since FliM is one of the components of the flagellar motor, we further investigated the integrity of flagella in mutated, complemented and WT strains. Immunofluorescence assays (IFA) were performed using major filament protein FlaB antibodies FIG. 4A-4C). Staining of the WT strain (FIG. 4B) revealed the presence of FlaB proteins from the extremities to the middle of the cell without overlapping, consistent with previous IFA experiments and the description of the flagella in *Leptospira*. Staining on complemented strain $702^{filM-/+}$ (FIG. 4C) was similar to WT. Mean FlaB stained flagella length of these two strains was 3.5 μm. However, $702^{fliM-}$ (FIG. 4A) showed either shorter flagella of approximately 1.3 μm or no flagella in 30% of the cells. In order to better characterize flagellar length, purified flagella of the 3 strains were observed by electron microscopy (FIGS. 4D-4I). For WT strains (FIGS. 4E and 4H), we observed intact coiled flagella of a median size of 3.2 μm in length, consistent with IFA experiment, and 20 nm in diameter. Observed flagella were composed of the basal body at one extremity and a filament displaying a thinner 15 nm diameter at the other extremity, probably due to the lack of sheath as already described in previous leptospiral flagella observations (14). A small number of broken flagella were observed, due to the fragility of the filaments. For $702^{filM-}$ (FIGS. 4D and 4G), all flagella were significantly shorter, with a median length of 0.7 μm. This observation was confirmed on 3 batches of flagella extracted from 3 independent cultures, excluding the fact that this shortness was only caused by flagella breaks.

To further characterize the short filaments on $702^{filM-}$, purified flagella were analyzed by electrophoresis. Coomassie staining revealed a different flagellar proteins content of $702^{filM-}$ compared to WT and complemented strains (FIG. 5A). In particular, we noticed less protein with an apparent molecular mass of about 30-40 kDa, corresponding to the size of previously described flagellar proteins (Liao, 2009, supra). Production of two major 30 kDa filament proteins, FlaA2 (LIC10787) and FlaB (LIC11531), was followed on Western Blot (FIGS. 5B and 5C). FlaA2 (FIG. 5B) and FlaB (FIG. 5C) protein levels were approximately 2.5 fold lower in $702^{filM-}$ flagella compared WT and $702^{filM-/+}$ strains, confirming an abnormally low quantity of flagellar proteins consistent with a shorter filament. The same reduction of FlaA2 and FlaB proteins expression was seen in whole cell lysates but not by qPCR, indicating that flagellar proteins content is lower in nonmotile strains than in WT but genes expression is not impaired. All together, these data show that fliM disruption leads to incomplete flagella assembly, and that these short flagella are not able to confer motility.

Motility is Essential for Virulence

Figure 6:
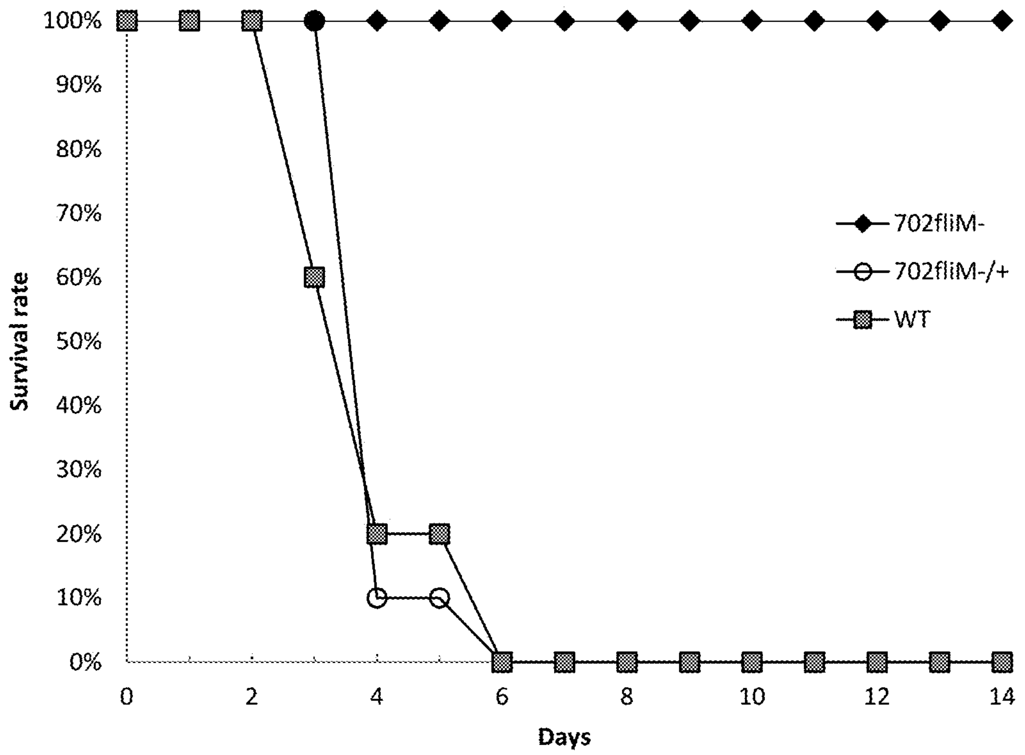
FIG. 6 is a graph representing hamster survival following injection with $10^8$ of either *L. interrrogans* serogroup autralis mutant strain $702^{fliM-}$, *L. interrrogans* serogroup autralis mutant strain $702^{fliM-/+}$ or wild type *L. interrrogans* serogroup autralis strain.

To investigate the role of motility in virulence, groups of five to ten hamsters were infected by intraperitoneal route with $10^8$ counts of $702^{filM-}$, $702^{filM-/+}$ or WT strains and followed for 14 days. While all $702^{filM-}$ infected hamsters survived, those receiving WT and $702^{fliM-/+}$ died within six days (FIG. 6). These data indicate that the non-motile $702^{filM-}$ is not virulent even at high infection dose, and that restoration of fliM and motility correlates with virulence restoration. Motility is therefore essential to virulence.

Live $702^{filM-}$ Vaccine Protects Against Homologous and Heterologous Challenge To investigate whether the $702^{filM-}$ strain may constitute a promising live canine vaccine candidate, we assessed protection of hamsters against homologous and heterologous challenges. Groups of 20 hamsters were vaccinated by intraperitoneal route with a single dose of $10^6$ live *L. interrogans* serogroup *Australis* $702^{filM-}$ or $10^8$ live saprophytic *L. biflexa* serovar Patoc or EMJH medium. Fourteen days after immunization, animals were challenged with virulent *L. interrogans* Australis or Icterohaemorrhagiae serogroup. and monitored for 21 days.

Figure 7:
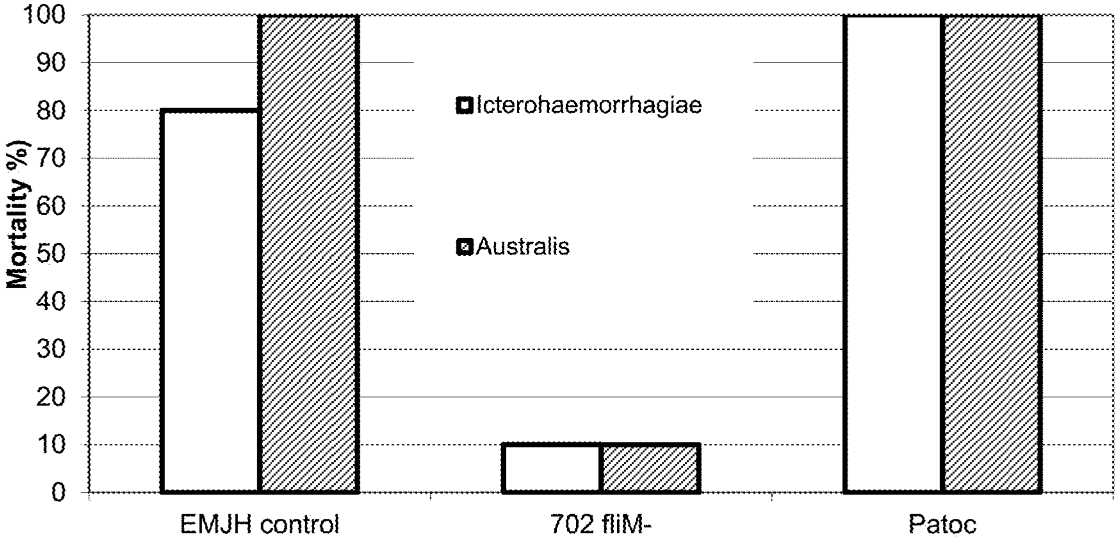
FIG. 7 is a graph showing the mortality of hamsters immunized with live $702^{fliM-}$ or Patoc or with culture medium alone and challenged with virulent strains of *L. interrrogans* serogroup Icterohaemorrhagiae (open bars) or Australis (hatched bars).

While 80 to 100% of EMJH or Patoc vaccinated animals died, 90% of the $702^{filM-}$ vaccinated hamsters survived in both challenge groups (see FIG. 7). These data indicate that the live non-motile $702^{filM-}$ virulence attenuated Serogroup Australis strain, but not the avirulent Patoc, used as live vaccine, is able to confer cross protective immunity against *L. interrogans* serovar icterohaemorrhagiae.

Discussion

Spirochetes are highly invasive bacteria, probably due to their remarkably efficient motility. In *Leptospira*, propulsion of the cells varies between 6 μm/s and 30 μm/s depending on viscosity and is conferred by only 2 flagella (Xu J, et al., 2015, Microbiol. Res., vol. 171, pp. 21-25; K. Takabe K, et al., 2013, Microbiol. Immunol., vol. 57, no. 3, pp. 236-239; Cameron C E, 2015, Curr. Top. Microbiol. Immunol., vol. 387, pp. 21-41). *B. burgorferi swims at similar speed but contains* 7 to 11 PFs, and *Critispira* has at least 100 PFs (Malawista S E et al., 2008, *PLoS ONE, vol.* 3, no. 2, p. e1633). The performance of the 2 *Leptospira flagella* may be due to a more complex structure provided by a higher number of genes related to motility. While 50 genes are referenced on *T. pallidium* and *B. burgorferi*, approximately 90 genes are present in *Leptospira* genome (A. L. T. O. do Nascimento ALTO et al., 2004, Braz. J. Med. Biol. Res., vol. 37, no. 4, pp. 459-477; M. Picardeau M et al., 2008, PLoS ONE, vol. 3, no. 2, p. e1607). Nonetheless, we showed in this study that a single nucleotide deletion in one of these genes, fliM, can destabilize the whole flagellar structure and suppress motility. This deletion was identified by whole genome sequencing and comparative genomics of strains $702^{filM-}$ and WT. A spontaneous deletion occurred in a homopolymer region close to the start of fliM gene, preventing expression of the protein. Complementation with functional fliM restored wild type phenotype, showing that this only mutation was responsible for $702^{filM-}$ defects. fliM is annotated as flagellar motor switch protein by inference with homologous genes in other bacterial species, but no studies confirmed this function so far on *Leptospira*. The attenuated mutant identified in this study is thus of great interest.

Phenotypic observations of the mutant revealed an atypical morphology. Cell extremities were impacted: the mutant strain lacked hook and spiral shaped ends. The main feature of the mutant is its motility loss. No translational shiftings were observed and only a minor population (approx. 2%) displayed slow and sporadic extremity movements not able to propel the cell. These findings indicate the impairment of *flagella* and motor rotation. We further characterized *flagella* and found that they were either absent or present in a truncated form in one or both extremities of our fliM-deficient mutant. Measures of their length by IFA and TEM revealed a reduced size of 2.5 to 4.5 fold compared to WT, consistent with a similar decrease of filament proteins expression noticed on western blots. However, when formed, *flagella* presented typical diameter and curvature compared to WT and previously published works (Nauman R K et al., 1969, J. Bacteriol., vol. 98, no. 1, p. 264), meaning that core and sheath of the *flagella* are not directly impaired. fliM is then required for *flagella* full-length and rotation, both essential for translational motility.

To further characterize the implication of *flagella* and motility in *Leptospira* pathogenicity, animal model (hamsters) were infected with the mutant strains. Infection experiments revealed the lack of virulence of the non-motile strain and restoration of full infectivity of complemented strain. This is the first report that we know of that direct implication of absence of motility and pathogenicity in *Leptospira* is shown, without possible polar effects. This finding is coherent with the idea that motility is essential for breaching the mucosal membranes, entering the tissues though damaged skin, dissemination in the host and organ penetration (Murray 2015, supra).

$702^{filM-}$ is a non-virulent strain that was isolated from a sick dog. It is likely that the animal has been originally infected by a virulent strain and that a point mutation have occurred following isolation with the mutated non-motile strain outgrowing the WT population in vitro. On the contrary, the Patoc strain belongs to a saprophytic, noninfectious species of *Leptospira*. Surprising, the results show that cross protection can only be achieved by using a virulence attenuated strain such as $702^{filM-}$, directly issued from a fully virulent isolate but not with an avirulent saprophytic strain.

In summary, genomic sequencing identified a spontaneous point mutation responsible for motility loss probably conferring selective advantage to *Leptospira* in in vitro media. This mutation in the fliM gene—which occurred during the culturing procedure—results in destabilization of the motor switch complex C-ring, leading to incomplete *flagella* assembly and defective rotation regulation, both essential for translational motility. In addition, apart from motility loss, improper *flagella* formation affects cell morphology and division. Additionally, with genetic complementation, we validate the direct implication of motility in pathogenicity of *Leptospira*, delivering knowledge on virulence mechanisms of these emerging zoonotic bacteria. Finally we demonstrated that the immobile mutant, directly issued from an originally virulent strain, is a suitable cross protective live vaccine candidate, with unique features that cannot be found using an avirulent saprophytic strain Example 2 Safety and Efficacy Study of Live Attenuated *L. interrogans* Vaccine in Homologous Challenge in Dogs The goal of the study is to evaluate the serological response (immunogenicity), safety/diffusibility and efficacy of a live attenuated *L. interrogans* vaccine in a homologous vaccination-challenge model in dogs.

The study was divided in 2 parts: vaccine phase from D0 to D37, and challenge phase from Tpre (=D38) to T26 (=D69) with challenge on T0 (2 weeks after the second vaccination). Sixteen six-month old, commercial source beagles were randomized to three groups as shown in Table 2 below. Dogs in Group A were vaccinated twice subcutaneously, 25 days apart on D0 and D25, with 1 mL of the live *L. interrogans* vaccine containing around $5\times10^7$ lepo/ml of the attenuated $702^{fliM-}$ strain. Dogs in Groups B (control group) and C (shedding control group) were not vaccinated. Dogs from groups A and C were housed together in order to determine potential shedding of the vaccinal strain. Dogs from group B were housed separately from the two other groups. The vaccinated dogs were monitored for injection site reactions (swelling, pain upon palpation), general condition (apathy, prostration) and body temperature. Blood samples were collected for serum ELISA (BS dry tube), hematobiochemical analysis (BS Hep-Li and BS EDTA), qPCR analysis of diffusibility or cellular immunity analysis (BS Hep-Na). Urine samples were collected for qPCR analysis of diffusibility. Dogs in group C were euthanized on D39 (T0) for post portem analysis of the presence of bacteria and tissue lesions in liver and kidneys. The schedule for sample collection in the vaccination phase is detailed in Table 2.

On D39 (T0), dogs in groups A and B were challenged by intraperitoneal route with a virulent strain *L. interrogans* serogroup Australis at dose of $5\times10^9$ lepo. Dogs from group C were not challenged but euthanized on D39. During the post challenge period the dogs were monitored daily for mortality, clinical signs (general condition, dehydration, ocular signs, vomiting, diarrheoa and cutaneo-mucosal signs), body temperature and weighing. Blood samples were collected for serum ELISA (BS dry tube), hematobiochemical analysis (BS Hep-Li and BS EDTA) and for qPCR analysis of leptospiremia (BS Hep-Na). Urine was collected for qPCR analysis of leptospiruria. Liver and kidneys were collected post mortem for qPCR analysis of the presence of bacteria as well as for tissue lesions observations. Surviving dogs in Group A and B were euthanized on T26. The schedule for sample collection in the vaccination phase is detailed in Table 2.1.

TABLE 2

Experimental design - vaccine phase

| Group | # of dog | Vaccine SC | serum ELISA (BS dry tube) | BS Hep-Li* + BS EDTA*** | qPCR (BS Hep-Na** + Urine) | BS Hep-Na (cellular immunity) | Challenge D39 = T0 |
|---|---|---|---|---|---|---|---|
| A vaccine | 8 | D0 & D25 1 ml/dog | D0, D7, D14, D25, prior to challenge | D0, D7, D14, D25, prior to challenge | D0, D2, D4 & D7 | D7, D14, D35 | D39 |
| B No vaccine | 6 | NA | prior to challenge | | NA | | D39 |
| C Control shedding | 2 | | D0, D7, D14, D25, prior to challenge | | D0, D2, D4 & D7 | | NA |

BS Hep-Li*: Blood collected in Lithium heparinised tubes for for biochemistry (urea, creatinine, ALT, AST, ALP).

BS Hep-Na**: Blood in Sodium heparinised tubes for detection of leptospires by qPCR and exploration of cellular immunity.

BS EDTA***: samples used for platelet count.

TABLE 2.1

Experimental design - challenge phase

| Group | # of dog | Challenge $4.5\times10^8$ lepo/ml IP | Clinical follow up | Blood sampling | Urine | Euthanize at the end of challenge |
|---|---|---|---|---|---|---|
| A Vaccinates | 8 | T0 (D39) 10 ml/dog | Clinical examination Daily T0 to T26 Body temperature Daily T0 to T7 Weight T0, T7, T14, T21, T26 | BS dry tube: T26 BS Hep-Li and BS EDTA: T3, T4, T5, T7 and T11 BS Hep-Na: T3, T4, T5, T7 and T11 | T3, T5, T7, T11, T14, T21, T26 | T26 |
| B Challenge controls | 6 | T0 (D39) 10 ml/dog | | | | |

The diffusibility/safety results are shown in Table 3 below. The results show that no leptospiruria were detected in vaccinated group (group A) and shedding dogs (group C). No adverse local or general signs were observed after vaccination in the vaccinated dogs.

TABLE 3

Diffusibility/safety results

| Group | Dog No. | Leptospiruria D 0 | D 2 | D 4 | D 7 |
|---|---|---|---|---|---|
| A vaccine | 1 | Negative | Negative | Negative | Negative |
| | 2 | Negative | Negative | Negative | Negative |
| | 3 | Negative | Negative | Negative | Negative |
| | 4 | Negative | Negative | Negative | Negative |
| | 5 | Negative | Negative | Negative | Negative |
| | 6 | Negative | Negative | Negative | Negative |
| | 7 | Negative | Negative | Negative | Negative |
| | 8 | Negative | Negative | Negative | Negative |
| B Control No vaccine | 1 | / | / | / | / |
| | 2 | / | / | / | / |
| | 3 | / | / | / | / |
| | 4 | / | / | / | / |
| | 5 | / | / | / | / |
| | 6 | / | / | / | / |
| C Control shedding | 1 | Negative | Negative | Negative | Negative |
| | 2 | Negative | Negative | Negative | Negative |

Figure 10:
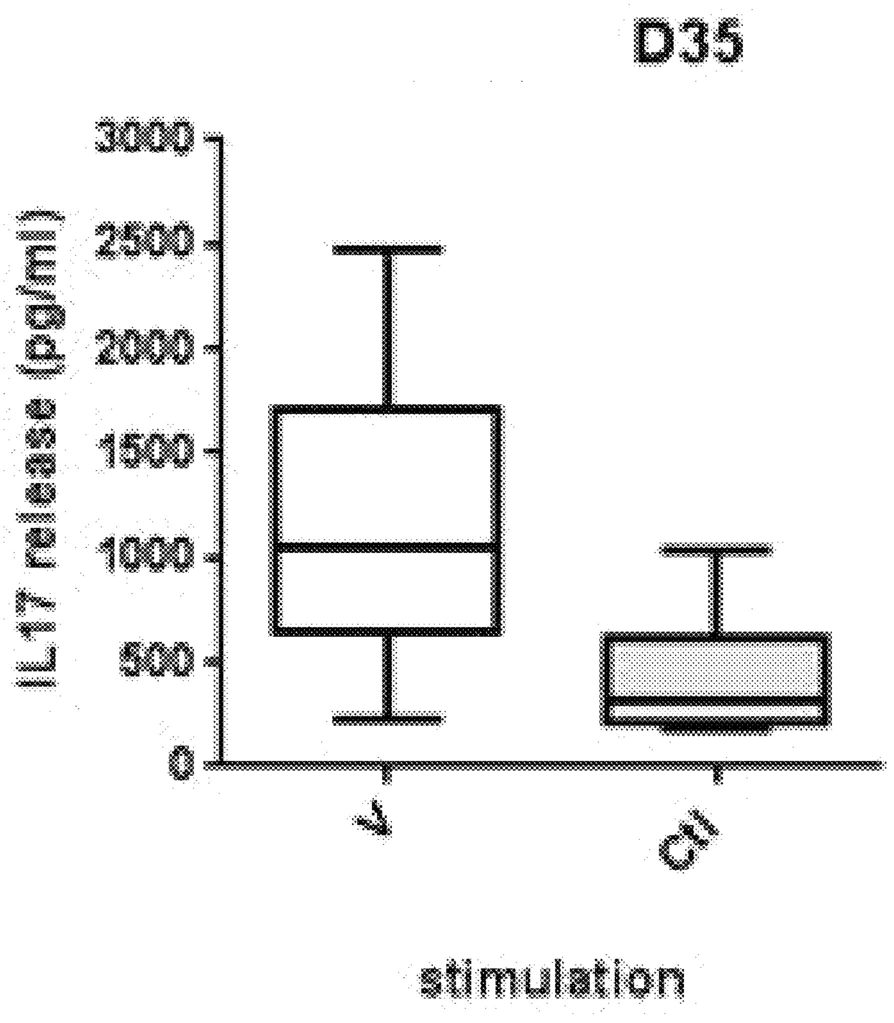
FIG. 10 depicts the I117 response in vaccinated and unvaccinated dogs.
Figure 11:
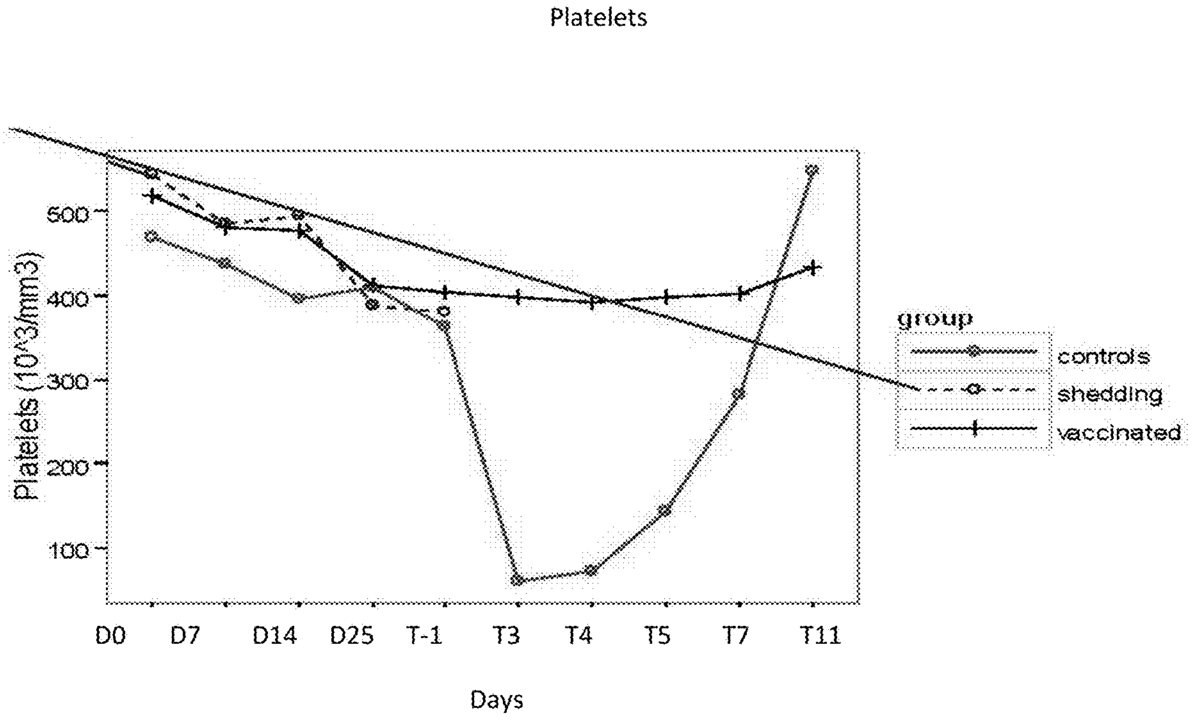
FIG. 11 depicts the platelets result in vaccinated, unvaccinated and shedding control dogs.
Figure 12:
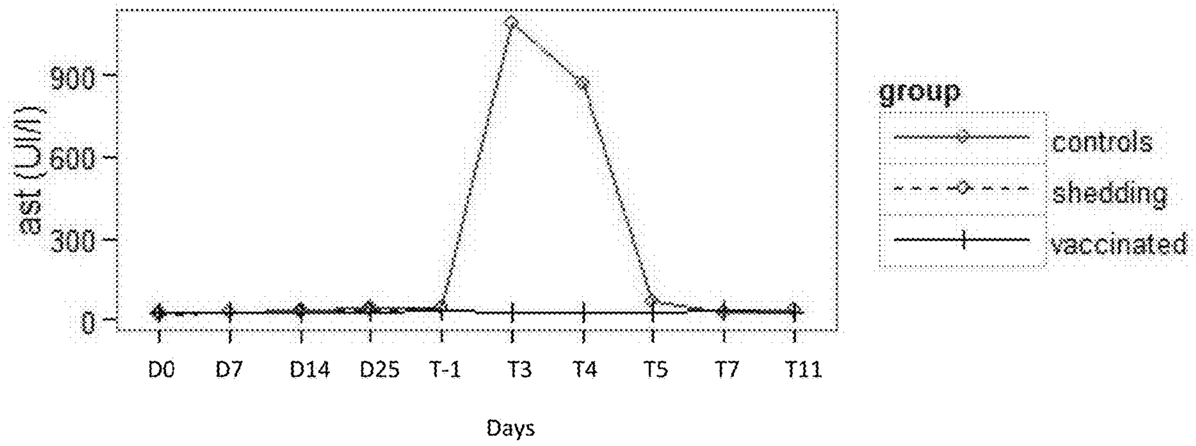
FIG. 12 depicts the ASAT result in vaccinated, unvaccinated and shedding control dogs.
Figure 13:
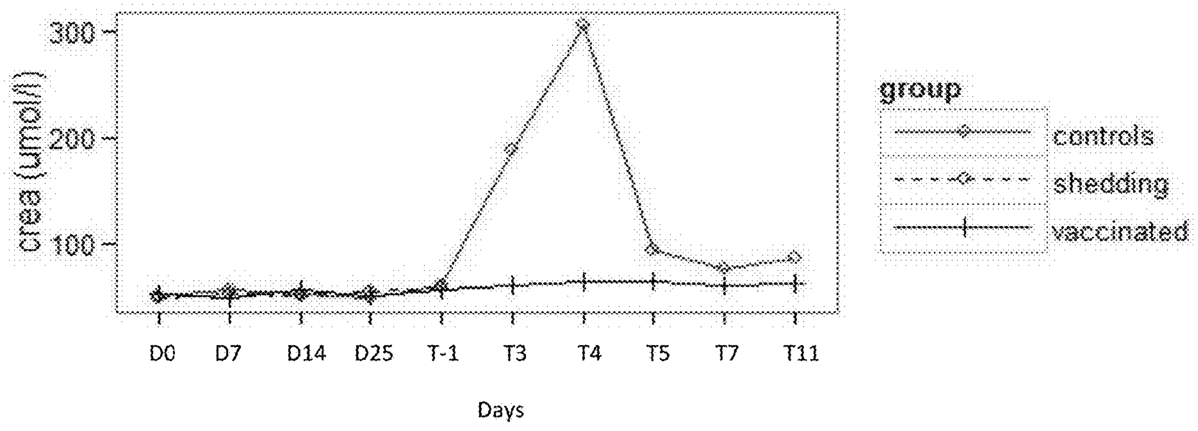
FIG. 13 depicts the creatinemia result in vaccinated, unvaccinated and shedding control dogs.
Figure 14:
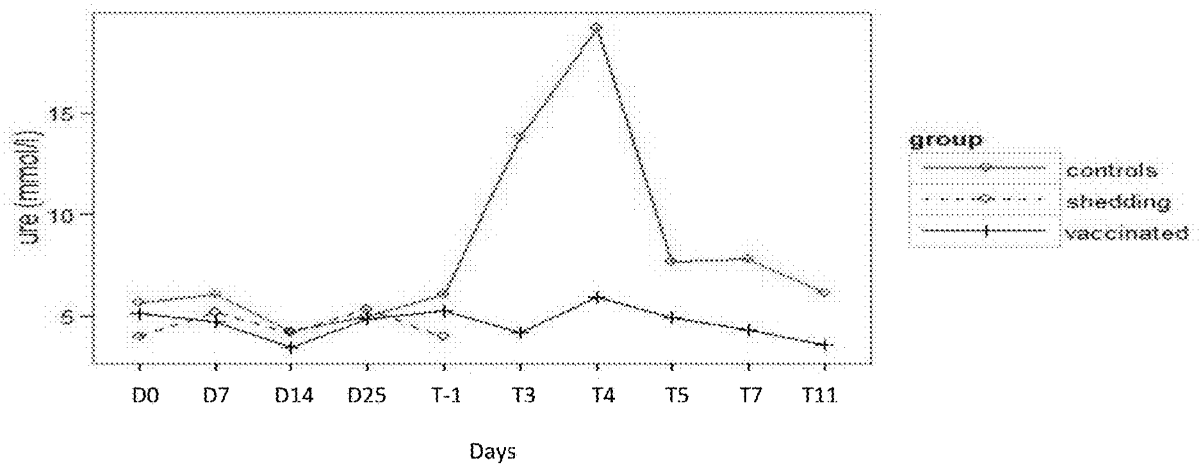
FIG. 14 depicts the uremia result in vaccinated, unvaccinated and shedding control dogs.
Figure 15:
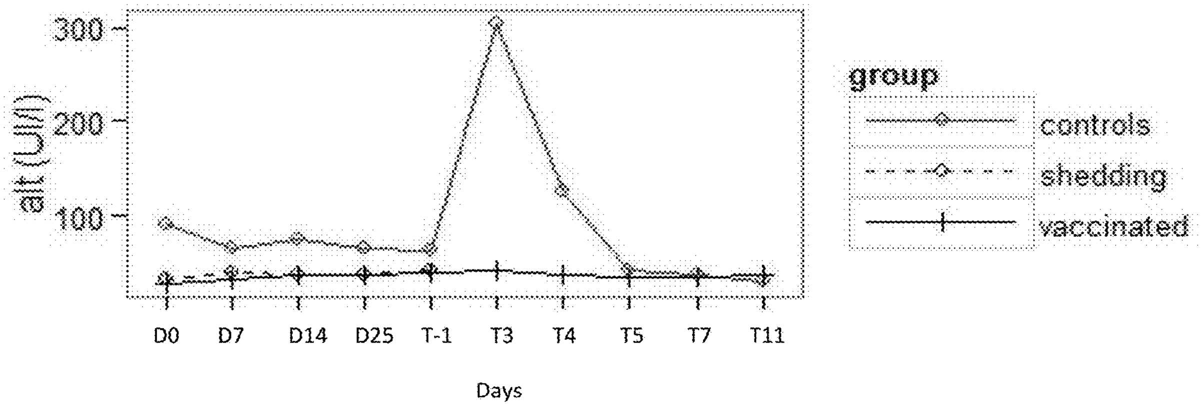
FIG. 15 depicts the ALAT result in vaccinated, unvaccinated and shedding control dogs.
Figure 16:
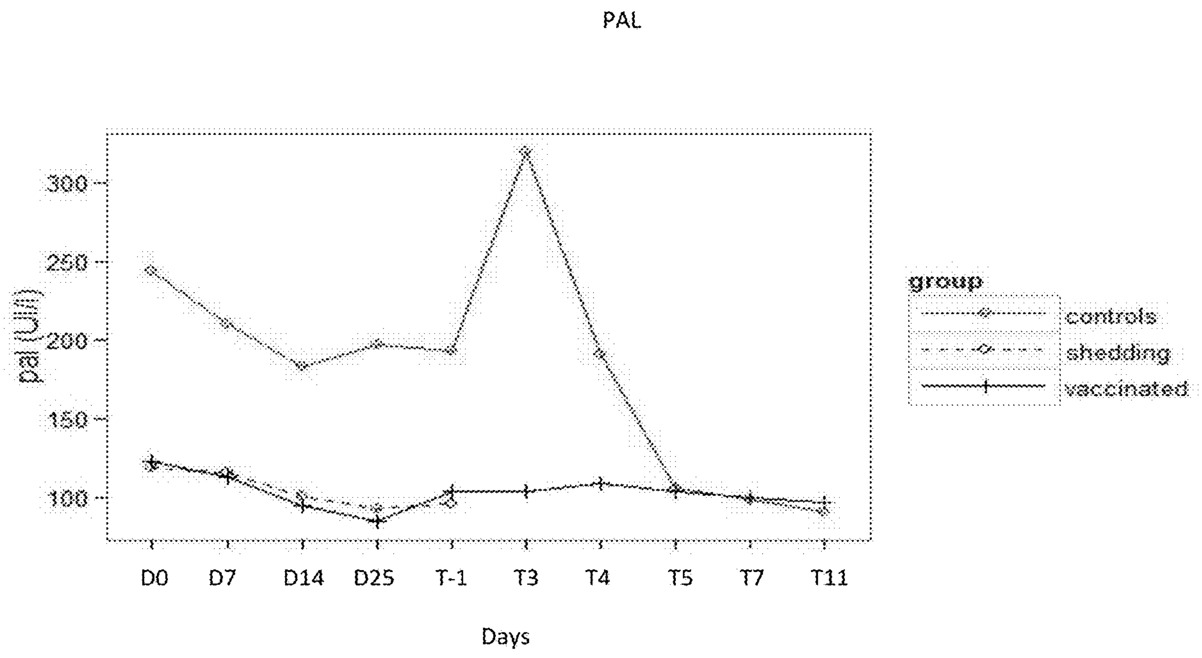
FIG. 16 depicts the PAL result in vaccinated, unvaccinated and shedding control dogs.

Cellular mediated immunity results are shown in FIG. 10. The *Leptospira* specific IL-17 response was detected in vaccinated dogs seven days after the $2^{nd}$ vaccine injection. No other cytokines (such as IFNg, TNFa, IL-6, IL8, IL10) were detected in vaccinated group in the in vitro PBMCs re-stimulation assays.

The efficacy results are shown in Table 4 below. The results demonstrated the excellent protection in the vaccinated dogs (group A) in terms of clinical signs: no dogs in group A (0/8) showed any clinical signs and five out of six dogs in group B (5/6) showed severe clinical signs. Also as shown in Table 4, no leptospiruria were detected in vaccinated dogs (group A) with only two dogs that were marginally positive at one time point, while the only dog in group B which did not show any clinical signs was positive in leptospiruria.

TABLE 4

Efficacy results

| Group | Dog No | Leptospiruria chal-lenge | T3 | T5 | T7 | T11 | T14 | T21 | T26 |
|---|---|---|---|---|---|---|---|---|---|
| A Vaccine | 1 | Neg | Neg | Neg | Neg | Neg | Neg | / | / |
| | 2 | Neg | Neg | Neg | Neg | Neg | Neg | / | / |
| | 3 | Neg | Neg | Neg | Neg | Neg | Neg | / | / |
| | 4 | Neg | Neg | Neg | Neg | Neg | Neg | / | / |
| | 5 | Neg | Neg | Neg | Neg | Neg | Neg | / | / |
| | 6 | Neg | Neg | Neg | Neg | Neg | + | / | / |
| | 7 | Neg | Neg | Neg | Neg | Neg | Neg | / | / |
| | 8 | Neg | Neg | + | Neg | Neg | Neg | / | / |
| B Control No vaccine | 1 | Neg | Neg | ++ | ++ | ++ | ++ | / | / |
| | 2 | Neg | / | / | / | / | / | / | / |
| | 3 | Neg | Neg | Euthanized on T4 | | | | | |
| | 4 | Neg | Euthanized on T3 | | | | | | |
| | 5 | Neg | Euthanized on T3 | | | | | | |
| | 6 | Neg | Euthanized on T3 | | | | | | |

TABLE 4-continued

Efficacy results

| Group | Dog No | Leptospiruria chal-lenge | T3 | T5 | T7 | T11 | T14 | T21 | T26 |
|---|---|---|---|---|---|---|---|---|---|
| C Control shed-ding | 1 | / | Euthanized on T0 | | | | | | |
| | 2 | / | Euthanized on T0 | | | | | | |

The results of hematobiological parameters (see FIGS. 11-16) showed that during the vaccination phase, there was no difference between controls (group B), vaccinated (group A) or shedding (group C) dogs. After challenge, significant effect on hematobiological parameters was observed in controls (group B) while there was no effect for vaccinated dogs (group A). In the control group (group B), all dogs died after challenge except one dog. The uremia and creatinemia parameters remains affected after T5 for this surviving dog in group B, which indicate that the dog's kidney was affected as reflected by leptospiruria.

The challenge was validated and was severe since five of the six control dogs were clinically diseased with severe clinical signs (prostration, digestive and cutaneo-mucosal signs) and alteration of biological parameters (urea, creatinine, AST, ALT, ALP and platelets) and had to be euthanized for ethical reasons on day 3 or 4 after challenge. These dogs had positive one or two blood samples, positive kidney samples and kidney and liver lesions.

After challenge, all vaccinated dogs remained in good general condition without any clinical signs or hyperthermia. No alteration of blood parameters was observed. *Leptospira* were not detected in blood and kidneys. Two vaccinated dogs had one marginally positive urine sample only, all urine samples remaining negative in the six other vaccinated dogs. No kidney or liver lesions were evidenced in all vaccinated dogs.

Protection against mortality, signs of disease (clinical signs, bodyweight, rectal temperature, biological parameters), infection, bacterial excretion, renal carnage and renal lesions was demonstrated in vaccinated dogs when compared to control dogs.

CONCLUSION

The results demonstrated that the live attenuated *L. interrogans* vaccine containing the attenuated $702^{filM-}$ strain is safe to use. When injected in the animals, it does not show any local or general signs, and does not have any effect on hematobiological parameters. There is no sign of shedding after the live attenuated vaccine is administered to the animals. The live attenuated *L. interrogans* vaccine ($702^{filM-}$ strain) also prevented mortality, clinical signs of the disease, infection, urinary excretion, renal carriage and renal lesions against a very virulent *L. interrogans* serogroup Australis challenge performed two weeks after the $2^{nd}$ injection of primary vaccination.

Example 3 Safety and Efficacy Study of Live Attenuated *L. interrogans* Vaccine Against Heterologous Challenges in Dogs The goal of the study is to evaluate the efficacy against heterologous challenge (onset of immunity) of a live attenuated *L. interrogans* vaccine in dogs.

Thirteen six-month old, commercial source beagles are randomized to two groups. Dogs in Group A are vaccinated twice subcutaneously, on D0 and D28, with 1 mL of the live *L. interrogans* vaccine containing $10^7$ lepo/ml of the attenuated $702^{filM-}$ strain. Dogs in Group B (control group) are not vaccinated.

On D42 (T0), each dog in groups A and B is challenged with a virulent strain *L. interrrogans* serogroup Icterohaemorrhagiae at a dose of $10^6$ lepo/ml. During the post challenge period the dogs are monitored daily for mortality, clinical signs (general condition, dehydration, ocular signs, vomiting, diarrheoa and cutaneo-mucosal signs), body temperature and weighing. Blood and urine are collected regularly throughout the vaccination phase for serological, hematobiochemical, leptospiremia, and leptospiruria analysis. Liver and kidneys are collected post mortem for analysis of the presence of bacteria as well as for tissue lesions observations. Surviving dogs in Group A and B are euthanized on T28.

The efficacy results show that the global clinical scores are significantly lower in the vaccinated dogs versus controls. Similarly the global biochemical and haematological scores, number of positive blood cultures per dog (leptospiremia), number of positive urine cultures per dog (leptospiruria), number of dogs with positive kidney culture and the number of dogs with kidney lesions are significantly lower in vaccinated groups when compared to controls.

CONCLUSION

The results demonstrate the live attenuated *L. interrogans* vaccine ($702^{filM-}$ strain) reduces mortality, clinical signs of the disease, infection, urinary excretion, renal carriage and renal lesions upon heterologous virulent *L. interrogans* serogroup Icterohaemorrhagiae challenge performed two weeks after the $2^{nd}$ injection of primary vaccination and provide cross protection against heterologous challenge.

Example 4 Deletion of fliM Gene

The goal of the study is to generate a recombinant and attenuated *L. interrogans*. by deleting the FliM gene encoding flits protein (SEQ ID NO:17) from *Leptospira interrogans* genome.

FliM gene encoding flits protein (SEQ ID NO:17) is deleted from *Leptospira interrogans* using two sequential steps of transformation.

A markerless mutation system for the pathogen *L. interrogans* is generated by developing tools allowing the performance of two sequential steps of transformation. By the first homologous recombination, the target gene fliM is replaced by a kanamycin resistance cassette, using an allelic exchange system as previously shown for ligB (Croda, J., et al., 2008, *Infect Immun* 76, 5826-5833). For the second transformation, the Flp recombinase system, a protein that promotes both inter- and intramolecular recombination (Hoang, T. T., et al., 1998, *Gene* 212, 77-86), is used as an efficient tool for the excision of DNA fragments inserted into the *Leptospira interrogans* bacterial chromosome.

Alternatively, the *S. cerevisiae* mitochondrial endonuclease I-SceI can be used to produce markerless deletion of fliM gene from *Leptospira interrogans* chromosome (Pósfai, G., et al., 1999, *Nucleic Acids Res* 27, 4409-4415)

The generated recombinant *Leptospira interrogans* where the fliM gene is deleted is stable and reliable, and is used as a live attenuated vaccine to in the efficacy studies against homologous and heterologous challenges in dogs as described in Example 5.

Example 5 Safety and Efficacy Study of Live Attenuated *L. interrogans* Vaccine Against Homologous and Heterologous Challenges in Dogs The goal of the studies is to evaluate the efficacy against homologous and heterologous challenge (onset of immunity) of a live attenuated *L. interrogans* vaccine in dogs. The live attenuated *L. interrogans* vaccine is generated in Example 4 where the FilM gene encoding fliM protein is deleted.

Commercial source beagles are randomized to two groups. Dogs in Group A are vaccinated twice subcutaneously, on D0 and D28, with 1 mL of the live *L. interrogans* vaccine containing $10^7$ lepo/ml of the attenuated *L. interrogans* strain. Dogs in Group B (control group) are not vaccinated.

In one study, on D42 (T0), each dog in groups A and B is challenged with a virulent strain *L. interrogans* serogroup Australis (homologous). In another study, on D42 (T0), each dog in groups A and B is challenged with a virulent strain *L. interrrogans* serogroup Icterohaemorrhagiae (heterologous). During the post challenge period the dogs are monitored daily for mortality, clinical signs (general condition, dehydration, ocular signs, vomiting, diarrheoa and cutaneo-mucosal signs), body temperature and weighing. Blood and urine are collected regularly throughout the vaccination phase for serological, hematobiochemical, leptospiremia, and leptospiruria analysis. Liver and kidneys are collected post mortem for analysis of the presence of bacteria as well as for tissue lesions observations. Surviving dogs in Group A and B are euthanized on T28.

The efficacy results show that the global clinical scores are significantly lower in the vaccinated dogs versus controls. Similarly the global biochemical and haematological scores, number of positive blood cultures per dog (leptospiremia), number of positive urine cultures per dog (leptospiruria), number of dogs with positive kidney culture and the number of dogs with kidney lesions are significantly lower in vaccinated groups when compared to controls.

CONCLUSION

The results demonstrate the live attenuated *L. interrogans* vaccine (fliM gene deleted) reduces mortality, clinical signs of the disease, infection, urinary excretion, renal carriage and renal lesions upon homologous virulent *L. interrogans* serogroup Australis and heterologous virulent *L. interrogans* serogroup Icterohaemorrhagiae challenges performed two weeks after the $2^{nd}$ injection of primary vaccination and provide protection against homologous challenge and cross protection against heterologous challenge.

What is claimed is:

1. A composition comprising a recombinant or an attenuated *Leptospira interrogans*, wherein the *Leptospira interrogans* comprises a mutated non-functional fliM gene, wherein the attenuated *Leptospira interrogans* is deposited under the CNCM deposit No. CNCM I-5132.

2. The composition of claim 1, wherein the composition further comprises at least one pharmaceutically or veterinarily acceptable carrier, vehicle, or excipient.

3. The composition of claim 1, wherein the composition comprises $10^7$ of the recombinant or the attenuated *Leptospira interrogans*.

4. A composition comprising a recombinant or an attenuated *Leptospira interrogans*, wherein the *Leptospira interrogans* comprises a mutated fliM gene, wherein the mutated, fliM gene encodes a mutated fliM protein, and wherein the C-terminal region of the fliM protein is deleted.

5. The composition of claim 4, wherein the fliM gene encodes a fliM protein having at least 90% sequence identity to SEQ ID NO: 18.

6. The composition of claim 4, wherein the fliM gene has at least 90% sequence identity to SEQ ID NO: 16.

7. The composition of claim 4, wherein the composition further comprises at least one pharmaceutically or veterinarily acceptable carrier, vehicle or excipient.

8. The composition of claim 4, wherein the composition comprises $10^7$ of the recombinant or the attenuated *Leptospira interrogans*.

9. A composition comprising a recombinant or an attenuated *Leptospira interrogans*, wherein the fliM gene is deleted from the *Leptospira interrogans*.

10. An isolated attenuated *Leptospira interrogans*, wherein the *Leptospira interrogans* comprises a mutated fliM gene wherein the C-terminal region of the protein is deleted.

11. The attenuated *Leptospira interrogans* of claim 10, wherein the fliM gene encodes a fliM protein having at least 90% sequence identity to SEQ ID NO: 18.

12. The attenuated *Leptospira interrogans* of claim 10, wherein the fliM gene has at least 90% sequence identity to SEQ ID NO: 16.

13. An isolated recombinant or an isolated attenuated *Leptospira interrogans*, wherein the fliM gene is deleted from the *Leptospira interrogans*.

14. An attenuated *Leptospira interrogans*, wherein the attenuated *Leptospira interrogans* is the strain deposited under the CNCM deposit No. CNCM I-5132.

15. A method of inducing a protective immune response against *Leptospira* infection in an animal comprising:

administering to the animal an effective amount of a composition comprising a recombinant or an attenuated *Leptospira interrogans*, wherein the *Leptospira interrogans* comprises a mutated non functional fliM gene, wherein the mutated, non functional fliM gene encodes a mutated fliM protein, and wherein the C-terminal region of the protein is deleted.

16. The method of claim 15, wherein the animal is a canine or a feline.

17. The method of claim 15, wherein the composition further comprises at least one pharmaceutically or veterinarily acceptable carrier, vehicle or excipient.

18. The method of claim 15, wherein the fliM gene encodes a fliM protein having at least 90% sequence identity to SEQ ID NO: 18.

19. The method of claim 15, wherein the fliM gene has at least 90% sequence identity to SEQ ID NO: 16.

20. The method of claim 15, wherein the composition comprising a recombinant or an attenuated *Leptospira interrogans*, wherein the *Leptospira interrogans* comprises a mutated non-functional fliM gene, and the *Leptospira interrogans* is the strain deposited under the CNCM deposit No. CNCM I-5132.

21. A method of inducing a protective immune response against *Leptospira* infection in an animal comprising:

administering to the animal an effective amount of a composition comprising a recombinant or an attenuated *Leptospira interrogans*, wherein the fliM gene is deleted from the *Leptospira interrogans*.

* * * * *

SEQUENCE LISTING

```
<160> NUMBER OF SEQ ID NOS: 20

<210> SEQ ID NO 1
<211> LENGTH: 22
```

-continued

<212> TYPE: DNA
<213> ORGANISM: artificial sequence
<220> FEATURE:
<223> OTHER INFORMATION: PflgA primer

<400> SEQUENCE: 1
taatacccga gcttcaagga ag 22

<210> SEQ ID NO 2
<211> LENGTH: 32
<212> TYPE: DNA
<213> ORGANISM: artificial sequence
<220> FEATURE:
<223> OTHER INFORMATION: FliMR2 primer

<400> SEQUENCE: 2
taacttcaat tctaatattc ttgttcagaa cg 32

<210> SEQ ID NO 3
<211> LENGTH: 26
<212> TYPE: DNA
<213> ORGANISM: artificial sequence
<220> FEATURE:
<223> OTHER INFORMATION: CF109 primer

<400> SEQUENCE: 3
caatcgtgct gaagaatctg aaagag 26

<210> SEQ ID NO 4
<211> LENGTH: 22
<212> TYPE: DNA
<213> ORGANISM: artificial sequence
<220> FEATURE:
<223> OTHER INFORMATION: CF099 primer

<400> SEQUENCE: 4
ctgtagcaca agcctgattc gc 22

<210> SEQ ID NO 5
<211> LENGTH: 21
<212> TYPE: DNA
<213> ORGANISM: artificial sequence
<220> FEATURE:
<223> OTHER INFORMATION: CF108 primer

<400> SEQUENCE: 5
tcccaagatg aaattgacgc g 21

<210> SEQ ID NO 6
<211> LENGTH: 25
<212> TYPE: DNA
<213> ORGANISM: artificial sequence
<220> FEATURE:
<223> OTHER INFORMATION: CF103 primer

<400> SEQUENCE: 6
ctactctttc accgatctga atggc 25

<210> SEQ ID NO 7
<211> LENGTH: 21
<212> TYPE: DNA
<213> ORGANISM: artificial sequence
<220> FEATURE:
<223> OTHER INFORMATION: flaB4F primer

<400> SEQUENCE: 7

-continued ctcatatttg cttgtgcgag c 21

<210> SEQ ID NO 8
<211> LENGTH: 27
<212> TYPE: DNA
<213> ORGANISM: artificial sequence
<220> FEATURE:
<223> OTHER INFORMATION: flaB4R primer

<400> SEQUENCE: 8
gaacgctact ggtttacaat tagttgc 27

<210> SEQ ID NO 9
<211> LENGTH: 20
<212> TYPE: DNA
<213> ORGANISM: artificial sequence
<220> FEATURE:
<223> OTHER INFORMATION: rpoBF primer

<400> SEQUENCE: 9
atggagcgga acgtgtagtc 20

<210> SEQ ID NO 10
<211> LENGTH: 20
<212> TYPE: DNA
<213> ORGANISM: artificial sequence
<220> FEATURE:
<223> OTHER INFORMATION: rpoBR primer

<400> SEQUENCE: 10
cttcgttcgt tccatgtcct 20

<210> SEQ ID NO 11
<211> LENGTH: 24
<212> TYPE: DNA
<213> ORGANISM: artificial sequence
<220> FEATURE:
<223> OTHER INFORMATION: FlimF primer

<400> SEQUENCE: 11
cgacacatat gacagaaatt ttat 24

<210> SEQ ID NO 12
<211> LENGTH: 32
<212> TYPE: DNA
<213> ORGANISM: artificial sequence
<220> FEATURE:
<223> OTHER INFORMATION: FlimR2 primer

<400> SEQUENCE: 12
taacttcaat tctaatattc ttgttcagaa cg 32

<210> SEQ ID NO 13
<211> LENGTH: 36
<212> TYPE: DNA
<213> ORGANISM: artificial sequence
<220> FEATURE:
<223> OTHER INFORMATION: fliM original sequence

<400> SEQUENCE: 13
gtttctgaac aaaaaaaagt aaagatctac gatttt 36

<210> SEQ ID NO 14
<211> LENGTH: 36
<212> TYPE: DNA
<213> ORGANISM: artificial sequence
<220> FEATURE:
<223> OTHER INFORMATION: fliM mutated sequence

<400> SEQUENCE: 14

```
gtttctgaac aaaaaaagta aagatctacg atttta                                  36
```

<210> SEQ ID NO 15
<211> LENGTH: 1023
<212> TYPE: DNA
<213> ORGANISM: artificial sequence
<220> FEATURE:
<223> OTHER INFORMATION: DNA of wild-type fliM gene in strain Australis733 (WT)

<400> SEQUENCE: 15

```
atgacagaaa ttttatccca agatgaaatt gacgcgttac ttagcgccat cagttccggt     60
gaagtaagcg aatcggatta tgcttccgtt tctgaacaaa aaaaagtaaa gatctacgat    120
tttaaacgtc cggataaatt ttcaaaagac caaatccgta ctttacaaat gatgcatgaa    180
acctttgcac gtcttgcaac cacagggctt tctgctcagc taagagcgct tgtttcggtt    240
cacgttgctt ctgtggatca gttgacttac gaagagttca ttcgttccat tccaaatccc    300
acaacacttg cagtaatcaa catggaccct cttagaggtt ctgcaatctt agaaattgat    360
ccatcaattt cttttacgat catcgatcgt ctgtttggtg gtaaaggaga acaggcaaaa    420
atttccaggg aactttctga aatagaaatg agcgtaatgg aaggaattat tgtaagaatt    480
ttaggaaaca tgagagaatc gtggtccaca gtgatagact taagacctag gcttggaaac    540
attgaaacaa accctcaatt tgctcaagta gttcctccaa acgacatggt ggttttgatt    600
actctggaaa ctaaaatcgg agaagtggaa gggatgacga atctttgtat tccttatatc    660
acgatcgaac cgatcatcaa taaactatca gcacaatatt ggtattcttc cattcgtaag    720
ggagaattgg atgaaaaccg tgccgtgatt caggaaagat tggatcaagt agccattcct    780
ttgattgcgg aagttgggtc tgtggacgtt tccattaacg attttatgaa tctttctatt    840
ggagatgtag taaaactcga aaacacttct acaagatcag agatgatcgt aaaagtagga    900
gaaagaaaaa agttcaaatg ccttcctgga agagtaggaa gcagactcgc cattcagatc    960
ggtgaaagag tagaagatat tccagatgaa cttttgggtt ctactcgttc tgaacaagaa   1020
tat                                                                 1023
```

<210> SEQ ID NO 16
<211> LENGTH: 1022
<212> TYPE: DNA
<213> ORGANISM: artificial sequence
<220> FEATURE:
<223> OTHER INFORMATION: mutated DNA of fliM gene in strain Australis702 (attenuated strain)

<400> SEQUENCE: 16

```
atgacagaaa ttttatccca agatgaaatt gacgcgttac ttagcgccat cagttccggt     60
gaagtaagcg aatcggatta tgcttccgtt tctgaacaaa aaaagtaaag atctacgatt    120
ttaaacgtcc ggataaattt tcaaaagacc aaatccgtac tttacaaatg atgcatgaaa    180
cctttgcacg tcttgcaacc acagggcttt ctgctcagct aagagcgctt gtttcggttc    240
acgttgcttc tgtggatcag ttgacttacg aagagttcat tcgttccatt ccaaatccca    300
caacacttgc agtaatcaac atggaccctc ttagaggttc tgcaatctta gaaattgatc    360
catcaatttc ttttacgatc atcgatcgtc tgtttggtgg taaaggagaa caggcaaaaa    420
```

-continued

```
tttccaggga actttctgaa atagaaatga gcgtaatgga aggaattatt gtaagaattt    480

taggaaacat gagagaatcg tggtccacag tgatagactt aagacctagg cttggaaaca    540

ttgaaacaaa ccctcaattt gctcaagtag ttcctccaaa cgacatggtg gttttgatta    600

ctctggaaac taaaatcgga gaagtggaag ggatgacgaa tctttgtatt ccttatatca    660

cgatcgaacc gatcatcaat aaactatcag cacaatattg gtattcttcc attcgtaagg    720

gagaattgga tgaaaaccgt gccgtgattc aggaaagatt ggatcaagta gccattcctt    780

tgattgcgga agttgggtct gtggacgttt ccattaacga ttttatgaat ctttctattg    840

gagatgtagt aaaactcgaa aacacttcta caagatcaga gatgatcgta aaagtaggag    900

aaagaaaaaa gttcaaatgc cttcctggaa gagtaggaag cagactcgcc attcagatcg    960

gtgaaagagt agaagatatt ccagatgaac ttttgggttc tactcgttct gaacaagaat   1020

at                                                                  1022


<210> SEQ ID NO 17
<211> LENGTH: 341
<212> TYPE: PRT
<213> ORGANISM: artificial sequence
<220> FEATURE:
<223> OTHER INFORMATION: fliM protein translated from wild-type DNA of
      fliM in strain Australis733 (WT)

<400> SEQUENCE: 17

Met Thr Glu Ile Leu Ser Gln Asp Glu Ile Asp Ala Leu Leu Ser Ala
1               5                   10                  15

Ile Ser Ser Gly Glu Val Ser Glu Ser Asp Tyr Ala Ser Val Ser Glu
            20                  25                  30

Gln Lys Lys Val Lys Ile Tyr Asp Phe Lys Arg Pro Asp Lys Phe Ser
        35                  40                  45

Lys Asp Gln Ile Arg Thr Leu Gln Met Met His Glu Thr Phe Ala Arg
    50                  55                  60

Leu Ala Thr Thr Gly Leu Ser Ala Gln Leu Arg Ala Leu Val Ser Val
65                  70                  75                  80

His Val Ala Ser Val Asp Gln Leu Thr Tyr Glu Glu Phe Ile Arg Ser
                85                  90                  95

Ile Pro Asn Pro Thr Thr Leu Ala Val Ile Asn Met Asp Pro Leu Arg
            100                 105                 110

Gly Ser Ala Ile Leu Glu Ile Asp Pro Ser Ile Ser Phe Thr Ile Ile
        115                 120                 125

Asp Arg Leu Phe Gly Gly Lys Gly Glu Gln Ala Lys Ile Ser Arg Glu
    130                 135                 140

Leu Ser Glu Ile Glu Met Ser Val Met Glu Gly Ile Ile Val Arg Ile
145                 150                 155                 160

Leu Gly Asn Met Arg Glu Ser Trp Ser Thr Val Ile Asp Leu Arg Pro
                165                 170                 175

Arg Leu Gly Asn Ile Glu Thr Asn Pro Gln Phe Ala Gln Val Val Pro
            180                 185                 190

Pro Asn Asp Met Val Val Leu Ile Thr Leu Glu Thr Lys Ile Gly Glu
        195                 200                 205

Val Glu Gly Met Thr Asn Leu Cys Ile Pro Tyr Ile Thr Ile Glu Pro
    210                 215                 220

Ile Ile Asn Lys Leu Ser Ala Gln Tyr Trp Tyr Ser Ser Ile Arg Lys
225                 230                 235                 240

Gly Glu Leu Asp Glu Asn Arg Ala Val Ile Gln Glu Arg Leu Asp Gln
```

-continued

```
                245                 250                 255

Val Ala Ile Pro Leu Ile Ala Glu Val Gly Ser Val Asp Val Ser Ile
            260                 265                 270

Asn Asp Phe Met Asn Leu Ser Ile Gly Asp Val Val Lys Leu Glu Asn
        275                 280                 285

Thr Ser Thr Arg Ser Glu Met Ile Val Lys Val Gly Glu Arg Lys Lys
    290                 295                 300

Phe Lys Cys Leu Pro Gly Arg Val Gly Ser Arg Leu Ala Ile Gln Ile
305                 310                 315                 320

Gly Glu Arg Val Glu Asp Ile Pro Asp Glu Leu Leu Gly Ser Thr Arg
                325                 330                 335

Ser Glu Gln Glu Tyr
            340


<210> SEQ ID NO 18
<211> LENGTH: 35
<212> TYPE: PRT
<213> ORGANISM: artificial sequence
<220> FEATURE:
<223> OTHER INFORMATION: truncated fliM protein translated from mutated
      DNA of fliM gene in strain Australis702 (attenuated strain)

<400> SEQUENCE: 18

Met Thr Glu Ile Leu Ser Gln Asp Glu Ile Asp Ala Leu Leu Ser Ala
1               5                   10                  15

Ile Ser Ser Gly Glu Val Ser Glu Ser Asp Tyr Ala Ser Val Ser Glu
            20                  25                  30

Gln Lys Lys
        35


<210> SEQ ID NO 19
<211> LENGTH: 12
<212> TYPE: PRT
<213> ORGANISM: artificial sequence
<220> FEATURE:
<223> OTHER INFORMATION: Translation of fliM original sequence

<400> SEQUENCE: 19

Val Ser Glu Gln Lys Lys Val Lys Ile Tyr Asp Phe
1               5                   10


<210> SEQ ID NO 20
<211> LENGTH: 6
<212> TYPE: PRT
<213> ORGANISM: artificial sequence
<220> FEATURE:
<223> OTHER INFORMATION: Translation of fliM mutated sequence

<400> SEQUENCE: 20

Val Ser Glu Gln Lys Lys
1               5
```